US012350265B2

(12) United States Patent
Bae et al.

(10) Patent No.: US 12,350,265 B2
(45) Date of Patent: Jul. 8, 2025

(54) PHARMACEUTICAL COMPOSITION FOR TREATING ACUTE MYELOID LEUKEMIA, CONTAINING FLT3 INHIBITOR AND CHEMOTHERAPEUTIC AGENTS

(71) Applicant: Hanmi Pharm. Co., Ltd., Hwaseong-si (KR)

(72) Inventors: In Hwan Bae, Hwaseong-si (KR); Ji Young Song, Hwaseong-si (KR); Jae Yul Choi, Hwaseong-si (KR); Young Gil Ahn, Hwaseong-si (KR)

(73) Assignee: Hanmi Pharm. Co., Ltd., Hwaseong-si (KR)

( * ) Notice: Subject to any disclaimer, the term of this patent is extended or adjusted under 35 U.S.C. 154(b) by 826 days.

(21) Appl. No.: 17/622,389

(22) PCT Filed: Jun. 25, 2020

(86) PCT No.: PCT/KR2020/008258
§ 371 (c)(1),
(2) Date: Dec. 23, 2021

(87) PCT Pub. No.: WO2020/262974
PCT Pub. Date: Dec. 30, 2020

(65) Prior Publication Data
US 2022/0354842 A1  Nov. 10, 2022

(30) Foreign Application Priority Data

Jun. 27, 2019  (KR) .................. 10-2019-0077302

(51) Int. Cl.
*A61K 31/496* (2006.01)
*A61K 31/506* (2006.01)
*A61P 35/02* (2006.01)

(52) U.S. Cl.
CPC .......... *A61K 31/496* (2013.01); *A61K 31/506* (2013.01); *A61P 35/02* (2018.01)

(58) Field of Classification Search
None
See application file for complete search history.

(56) References Cited

U.S. PATENT DOCUMENTS

| 8,461,170 | B2 * | 6/2013 | Aquila ................ C07D 401/14 544/333 |
| 8,492,429 | B2 | 7/2013 | Griffin et al. |
| 9,796,712 | B2 | 10/2017 | Huang et al. |
| 10,280,154 | B2 | 5/2019 | Ham et al. |
| 10,519,141 | B2 | 12/2019 | Ham et al. |
| 10,870,639 | B2 | 12/2020 | Bae et al. |
| 11,292,786 | B2 | 4/2022 | Bae et al. |
| 2009/0318446 | A1 | 12/2009 | Fischer et al. |
| 2010/0056467 | A1 | 3/2010 | Griffin et al. |
| 2010/0104567 | A1 | 4/2010 | Shiotsu et al. |
| 2010/0249176 | A1 | 9/2010 | Barrow et al. |
| 2011/0009365 | A1 | 1/2011 | Dubois et al. |
| 2011/0015173 | A1 | 1/2011 | Florjancic et al. |
| 2011/0183975 | A1 | 7/2011 | Goto et al. |
| 2013/0137650 | A1 | 5/2013 | Armstrong et al. |
| 2017/0029413 | A1 | 2/2017 | Holladay et al. |
| 2017/0216302 | A1 | 8/2017 | Seki |
| 2017/0281566 | A1 | 10/2017 | Ciceri et al. |
| 2017/0355696 | A1 | 12/2017 | Jiang |
| 2018/0071290 | A1 | 3/2018 | Cai et al. |
| 2019/0031643 | A1 | 1/2019 | Ham et al. |
| 2019/0117649 | A1 | 4/2019 | Bahceci et al. |
| 2019/0125747 | A1 | 5/2019 | Rezaei et al. |
| 2019/0127353 | A1 | 5/2019 | Ham et al. |
| 2019/0298719 | A1 | 10/2019 | Ferretti et al. |
| 2019/0314380 | A1 | 10/2019 | Falini et al. |
| 2020/0031806 | A1 | 1/2020 | Bae et al. |
| 2020/0062775 | A1 | 2/2020 | Xue et al. |
| 2020/0206266 | A1 | 7/2020 | Hudecek et al. |
| 2020/0255410 | A1 | 8/2020 | Bae et al. |
| 2020/0360372 | A1 | 11/2020 | Bahceci et al. |
| 2022/0110913 | A1 | 4/2022 | Bae et al. |
| 2023/0002358 | A1 | 1/2023 | Bae et al. |
| 2024/0423979 | A1 | 12/2024 | Kim et al. |

FOREIGN PATENT DOCUMENTS

| CN | 101111490 A | 1/2008 |
| CN | 101622015 A | 1/2010 |
| CN | 102471339 A | 5/2012 |
| CN | 108883109 A | 11/2018 |
| CN | 113166110 A | 7/2021 |
| EA | 201692261 A1 | 5/2017 |
| EA | 202191984 A1 | 11/2021 |
| EA | 039868 B1 | 3/2022 |
| EP | 2133095 A1 | 12/2009 |
| EP | 3514153 A1 | 7/2019 |
| EP | 3928780 A1 | 12/2021 |

(Continued)

OTHER PUBLICATIONS

International Search Report and Written Opinion for International Patent Application No. PCT/KR2020/013188 dated Jan. 6, 2021, and English translation, 24 pages.
Advani, Anjali S., "FL T3 and Acute Myelogenous Leukemia: Biology, Clinical Significance and Therapeutic Applications", Current Pharmaceutical Design, 2005, vol. 11, No. 26, pp. 3449-3457.
Araki, Shinsuke et al., "Inhibitors of CLK Protein Kinases Suppress Cell Growth and Induce Apoptosis by Modulating Pre-mRNA Splicing", PLOS One, Jan. 12, 2015, vol. 10, 18 pages.
Benson et al., "Identification of Telmisartan as a Unique Angiotensin II Receptor Antagonist With Selective PPARγ-Modulating Activity", Hypertension, May 2004, vol. 43, pp. 993-1002.
Buglio, D., et al., "Essential Role of TAK1 in Regulating Mantle Cell Lymphoma Survival," Blood, 2012, vol. 120(2), pp. 347-355.

(Continued)

*Primary Examiner* — Brian J Davis
(74) *Attorney, Agent, or Firm* — COOLEY LLP

(57) ABSTRACT

Provided are: a pharmaceutical composition for treating myeloid leukemia (AML), and a method for treating acute myeloid leukemia using same, the pharmaceutical composition comprising a therapeutically effective combination of an Fms-like tyrosine kinase-3 (FLT3) inhibitor or pharmaceutically acceptable salt or solvate thereof, and a chemotherapeutic agent or pharmaceutically acceptable salt or solvate thereof.

21 Claims, 1 Drawing Sheet

(56) References Cited

FOREIGN PATENT DOCUMENTS

| | | |
|---|---|---|
| JP | 2008526824 A | 7/2008 |
| JP | WO2008111441 A1 | 6/2010 |
| JP | 2011500808 A | 1/2011 |
| JP | 2011510052 A | 3/2011 |
| JP | 2012521435 A | 9/2012 |
| JP | 2012533553 A | 12/2012 |
| JP | 2017510651 A | 4/2017 |
| JP | 2018535975 A | 12/2018 |
| JP | 2019531315 A | 10/2019 |
| JP | 6608565 B2 | 11/2019 |
| KR | 20080021126 A | 3/2008 |
| KR | 20090087094 A | 8/2009 |
| KR | 20090115866 A | 11/2009 |
| KR | 20170012766 A | 2/2017 |
| KR | 101755725 B1 | 7/2017 |
| KR | 20170101908 A | 9/2017 |
| KR | 20170123602 A | 11/2017 |
| KR | 20180086768 A | 8/2018 |
| KR | 20180088317 A | 8/2018 |
| KR | 20180117710 A | 10/2018 |
| KR | 20180124055 A | 11/2018 |
| KR | 101954370 B1 | 3/2019 |
| KR | 20190084292 A | 7/2019 |
| KR | 20200016567 A | 2/2020 |
| KR | 102110573 B1 | 5/2020 |
| KR | 20200102948 A | 9/2020 |
| MX | 2019008808 A | 9/2019 |
| TW | 201829396 A | 8/2018 |
| WO | WO-2006075152 A1 | 7/2006 |
| WO | WO-2006135639 A1 | 12/2006 |
| WO | WO-2008067280 A2 | 6/2008 |
| WO | WO-2009054983 A1 | 4/2009 |
| WO | WO-2009109710 A1 | 9/2009 |
| WO | WO-2010049731 A1 | 5/2010 |
| WO | WO-2010051781 A1 | 5/2010 |
| WO | WO-2010111172 A1 | 9/2010 |
| WO | WO-2011008915 A1 | 1/2011 |
| WO | WO-2011162515 A2 | 12/2011 |
| WO | WO-2013014448 A1 | 1/2013 |
| WO | WO-2013146963 A1 | 10/2013 |
| WO | WO-2014155300 A2 | 10/2014 |
| WO | WO-2015154038 A1 | 10/2015 |
| WO | WO-2015154039 A2 | 10/2015 |
| WO | WO-2015154039 A3 | 12/2015 |
| WO | WO-2016029839 A1 | 3/2016 |
| WO | WO-2015154039 A8 | 10/2016 |
| WO | WO-2017083592 A1 | 5/2017 |
| WO | WO-2017157813 A1 | 9/2017 |
| WO | WO-2017170348 A1 | 10/2017 |
| WO | WO-2018002217 A1 | 1/2018 |
| WO | WO-2018118842 A1 | 6/2018 |
| WO | WO-2018134213 A1 | 7/2018 |
| WO | WO-2018139903 A1 | 8/2018 |
| WO | WO-2018156578 A1 | 8/2018 |
| WO | WO-2019164846 A1 | 8/2019 |
| WO | WO-2020014643 A1 | 1/2020 |
| WO | WO-2020022600 A1 | 1/2020 |
| WO | WO-2020171646 A1 | 8/2020 |
| WO | WO-2020171649 A1 | 8/2020 |
| WO | WO-2020262974 A1 | 12/2020 |
| WO | WO-2021066443 A1 | 4/2021 |
| WO | WO-2021159993 A1 | 8/2021 |
| WO | WO-2022098083 A1 | 5/2022 |
| WO | WO-2023068858 A1 | 4/2023 |
| WO | WO-2024096708 A1 | 5/2024 |
| WO | WO-2024124199 A1 | 6/2024 |
| WO | WO-2024248513 A1 | 12/2024 |

OTHER PUBLICATIONS

Carter et al., "Synergistic Targeting of AML Stem/Progenitor Cells With IAP Antagonist Birinapant and Demethylating Agents", JNCI, Feb. 5, 2014, 106(2): djt440, 12 pages.

Extended European Search Report for European Patent Application No. 18744290.0 dated Mar. 31, 2020, 7 pages.

Extended European Search Report for European Patent Application No. 19841611.7 dated Mar. 17, 2022, 11 pages.

Extended European Search Report for European Patent Application No. 20201112.8 dated Feb. 5, 2021, 6 pages.

Huang, et al., "Synthesis and biological study of 2-amino-4-aryl-5-chloropyrimidine analogues as inhibitors of VEGFR-2 and cyclin dependent kinase 1 (CDK1)". Bioorganic & Medicinal Chemistry Letters (Apr. 15, 2007); 17(8): 2179-2183. Epub Feb. 2, 2007.

International Preliminary Report on Patentability for International Patent Application No. PCT/KR2020/002536 mailed Aug. 10, 2021, and English translation, 10 pages.

International Preliminary Report on Patentability for International Patent Application No. PCT/KR2020/008258 mailed Dec. 28, 2021, and English translation, 8 pages.

International Search Report and Written Opinion for International Patent Application No. PCT/KR2020/013188 dated Jun. 4, 2020, and English translation of ISR, 15 pages.

International Search Report for International Patent Application No. PCT/KR2018/001193 dated May 2, 2018, and English translation, 7 pages.

International Search Report for International Patent Application No. PCT/KR2019/001737 mailed May 8, 2019, 4 pages.

International Search Report for International Patent Application No. PCT/KR2020/002536 dated Jun. 4, 2020, and English translation, 5 pages.

International Search Report for International Patent Application No. PCT/KR2020/008258 dated Sep. 22, 2020, and English translation, 7 pages.

Khurana and Shafer, "MDM2 antagonists as a novel treatment option for acute myeloid leukemia: perspectives on the therapeutic potential of idasanutlin (RG7388)". Onco Targets Ther. (2019); 12: 2903-2910. Epub Apr. 16, 2019.

Kiyoi et al., "FLT3 mutations in acute myeloid leukemia: Therapeutic paradigm beyond inhibitor development.". Cancer Science, Feb. 2020; 111(2): 312-322.

Kliche, Stefanie et al., "VEGF Receptor Signaling and Endothelial Function", IUBMB Life, 2001, vol. 51, pp. 61-66, 6 pages.

Konig et al., "The Combination Of FL T3 Inhibition and Hypomethylation Confers Synergistic Anti-Leukemic Effects On FL T3/ITD Positive AML Cell Lines and Primary Cells", Blood, Nov. 15, 2013, 122(21): 3965, 3 pages.

Lee et al., "FL T3MutationsConfer Enhanced Proliferation and Survival Properties to Multipotent Progenitors in a Murine Model of Chronic Myelomonocytic Leukemia", Cancer Cell, Oct. 2007, vol. 12, pp. 367-380.

Liu et al., "Syk inhibitors in clinical development for hematological malignancies", Journal of Hematology and Oncology, 2017, 10: 145, 7 pages.

McMahon et al., "Clonal Selection with RAS Pathway Activation Mediates Secondary Clinical Resistance to Selective FLT3 Inhibition in Acute Myeloid Leukemia". Cancer Discov, 2019, 9 (8): 1050-1063.

Melnikova, Irena et al., "Targeting protein kinases", Nature Reviews Drug Discovery, Dec. 2004, pp. 993-994, 2 pages.

Moore et al., "Selective FL T3 inhibition of FL T3-ITD t acute myeloid leukaemia resulting in secondary D835Y mutation: a model for emerging clinical resistance patterns", Leukemia, 2012, pp. 1462-1470.

Paccez, Juliano D. et al., "The receptor tyrosine kinase Axl in cancer: biological functions and therapeutic implications", International Journal of Cancer, 2014, 39 pages, vol. 134.

Seipel et al., "Pabst T. MDM2-and FLT3-inhibitors in the treatment of FLT3-ITD acute myeloid leukemia, specificity and efficacy of NVP-HDM201 and midostaurin". Haematologica, Nov. 2018; 103(11): 1862-1872. Pre-published: Jul. 5, 2018.

Simons, Michael et al., "Mechanisms and regulation of endothelial VEGF receptor signalling", Nature Reviews Molecular Cell Biology, Oct. 2016, vol. 17, pp. 611-625, 15 pages.

(56) References Cited

OTHER PUBLICATIONS

Smith et al., "Validation of ITD mutations in FLT3 as a therapeutic target in human acute myeloid leukaemia", Nature, 2012, vol. 000, p. 1-6.
Sun, Xianglan et al., :"The regulation and function of the NUAK family", Journal of Molecular Endocrinology, 2013, 9 pages, vol. 51.
Ueno, et al., "Evaluation of gilteritinib in combination with chemotherapy in preclinical models of FLT3-ITD+ acute myeloid leukemia". Oncotarget (2019); 10(26): 2530-2545.
Wang et al., "Crenolanib, a Type I FLT3 Tki, Can be Safely Combined with Cytarabine and Anthracycline Induction Chemotherapy and Results in High Response Rates in Patients with Newly Diagnosed FLT3 Mutant Acute Myeloid Leukemia (AML)". Blood. Jan. 1, 2016; 128(22): 1071, 4 pages.
Weisberg et al., "Drug resistance in mutant FL T3-positive AML", Oncogene, Sep. 2010, 29(37): 5120-5134.
Weisberg et al., "Potentiation of antileukemic therapies by Smac mimetic, LBW242: effects on mutant FL T3-expressing cells", Molecular Cancer Therapeutics, Jul. 2007, 6(7): 1951-1961.
Written Opinion for International Patent Application No. PCT/KR2018/001193 dated May 2, 2018, and English translation, 12 pages.
Written Opinion for International Patent Application No. PCT/KR2019/001737 mailed May 8, 2019, 4 pages.
Written Opinion for International Patent Application No. PCT/KR2020/002536 dated Jun. 4, 2020, and English translation, 16 pages.
Written Opinion for International Patent Application No. PCT/KR2020/008258 dated Jun. 4, 2020, and English translation, 13 pages.
Wu, Xiaoliang et al., "AXL kinase as a novel target for cancer therapy", Oncotarget, Oct. 16, 2014, vol. 20, No. 5, pp. 9546-9563, 18 pages.
Yamada et al., IL-1 Induced Chemokine Production Through the Association of Syk with TNF Receptor-Associated Factor-6 in Nasal Fibroblast Lines, Journal of Immunology, Jul. 1, 2001, pp. 283-288.
Zhao et al., "The regulation of MDM2 oncogene and its impact on human cancers". Acta Biochim Biophys Sin. Mar. 1, 2014; 46(3): 180-189.
Co-pending U.S. Appl. No. 18/251,827, inventors Bae; In Hwan et al., filed May 4, 2023.
Edwards, D., et al., "CPX-351 works synergistically in combination with FLT3 inhibitors against AML with FLT3-ITD", Cancer Research Jul. 2017; vol. 77, No. Suppl. 13, p. 1087, & Annual Meeting of the American Association for Cancer Research (AACR); Washington, DC, USA; Apr. 1-5, 2017, 2 pages.
Extended European Search Report for European Application No. EP20200833623 dated Jun. 5, 2023, 9 pages.
Schittenhelm, M., et al., "The FLT3 1-15 inhibitor tandutinib (formerly MLN518) has sequence-independent synergistic effects with cytarabine and daunorubicin", Cell Cycle. Aug. 15, 2009; 8(16): 2621-2630. Epub Aug. 24, 2009.
International Preliminary Report on Patentability for International Patent Application No. PCT/KR2021/015794 dated May 8, 2023, and English translation, 4 pages.
International Search Report and English translation for International Patent Application No. PCT/KR2021/015794 mailed Feb. 10, 2022, and English translation, 9 pages.
Written Opinion for International Patent Application No. PCT/KR2021/015794 mailed Feb. 10, 2022, and English translation 6 pages.
[Author Unknown] "Khimicheskiy entsiklopedicheskiy slovar" (Chemical Encyclopedic Dictionary), Moscow: «Sovetskaya Entsiklopediya», 1983, pp. 130-131, and English translation of relevant portion, 7 pages.

Bastin et al., "Salt Selection and Optimisation Procedures for Pharmaceutical New Chemical Entities," Organic Process Research and Development (Jul. 19, 2000); 4(5): 427-435.
Belikov, V.G ,"Pharmaceutical Chemistry. Chapter 2.6 Relationship between the chemical structure, properties of substances and their effect on the body—M," MEDpress-inform, 2007, pp. 27-29, and English translation, 14 pages.
Kümmerer , K., et al., "Pharmaceuticals in the Environment," Annual Review of Environment and Resources (2010); vol. 35, pp. 57-75. Epub Aug. 18, 2010.
Pokrovsky, V.I., "Small Medical Encyclopedia," Medicine, 1996, V5, pp. 90-96, and English translation of relevant portion, 12 pages.
Extended European Search Report for European Application No. 20759712.1 dated Nov. 4, 2022, 10 pages.
Daver, N., et al., "Targeting FLT3 Mutations in AML: Review of Current Knowledge and Evidence," Leukemia (Jan. 16, 2019); 33(2): 299-312. Epub Jan. 16, 2019.
Chang, E. et al., "The combination of FLT3 and DNA methyltransferase inhibition is synergistically cytotoxic to FLT3/ITD acute myeloid leukemia cells". Leukemia, Dec. 21, 2015, vol. 30, No. 5, pp. 1025-1032.
Ueno, Y. et al., "Gilteritinib (ASP2215), a Novel FLT3/AXL Inhibitor: Preclinical Evaluation in Combination with Azacitidine in Acute Myeloid Leukemia". Blood, Dec. 2, 2016, vol. 128, No. 22, p. 2830, 4 pages.
Wu, M. et al., "FLT3 inhibitors in acute myeloid leukemia". Journal of Hematology & Oncology, Dec. 4, 2018, vol. 11, No. 1, pages Article No. 133, 11 pages.
Brinton et al., "Synergistic effect of BCL2 and FLT3 co-inhibition in acute myeloid leukemia", J Hematol Oncol, 2020; 13: 139, 10 pages; doi:10.1186/s13045-020-00973-4.
Edwards et al., "Effective Combination of CPX/351 with FLT3 Inhibitors in AML Blasts Harboring the FLT3-ITD Mutation", Blood Dec. 2, 2016; 128 (22): 5124, 2 pages. Abstract Only.
Extended European Search Report for European Patent Application No. 21889548.0, by Hanmi Pharm. Co., Ltd., mailed Sep. 12, 2024, 9 pages.
International Preliminary Report on Patentability for International Application No. PCT/KR2022/016095, including Notification Concerning Transmittal, by Hanmi Pharm. Co., Ltd., mailed May 2, 2024, 8 pages.
International Preliminary Report on Patentability for International Application No. PCT/KR2019/001737, with Notification of Transmittal, by Hanmi Pharm. Co., Ltd., mailed Feb. 4, 2021, 9 pages.
International Search Report and Written Opinion for International Application No. PCT/KR2022/016095, with Notification of Transmittal, by Hanmi Pharm. Co., Ltd., mailed Jan. 27, 2023, 12 pages.
International Search Report and Written Opinion for International Application No. PCT/US2023/083227, with Notification of Transmittal, by Aptose Biosciences Inc., mailed Apr. 2, 2024, 13 pages.
International Search Report and Written Opinion for International Application No. PCT/KR2023/017598, including Notification of Transmittal, by Hanmi Pharm. Co., Ltd., mailed Feb. 14, 2024, 16 pages.
International Search Report and Written Opinion for International Application No. PCT/KR2024/007424, with Notification of Transmittal, by Hanmi Pharm. Co., Ltd., mailed Sep. 11, 2024, 16 pages.
Luppi et al., "Novel Agents for Acute Myeloid Leukemia", Cancers, Nov. 9, 2018; 10(11): 429, 18 pages.
Wu et al., "Current status of treatment and research progress of new drugs for adult acute myeloid leukemia", Pharmaceutical and Clinical Research, Aug. 15, 2018; 4: 281-286 (Chinese with English abstract on p. 286).
Zhu et al., "FLT3 tyrosine kinase inhibitors synergize with BCL-2 inhibition to eliminate FLT3/ITD acute leukemia cells through BIM activation", Signal Transduction and Targeted Therapy, 2021, [Epub] May 24, 2021; 6: 186, doi10.1038/s41392-021-00578-4; 11 pages.

\* cited by examiner

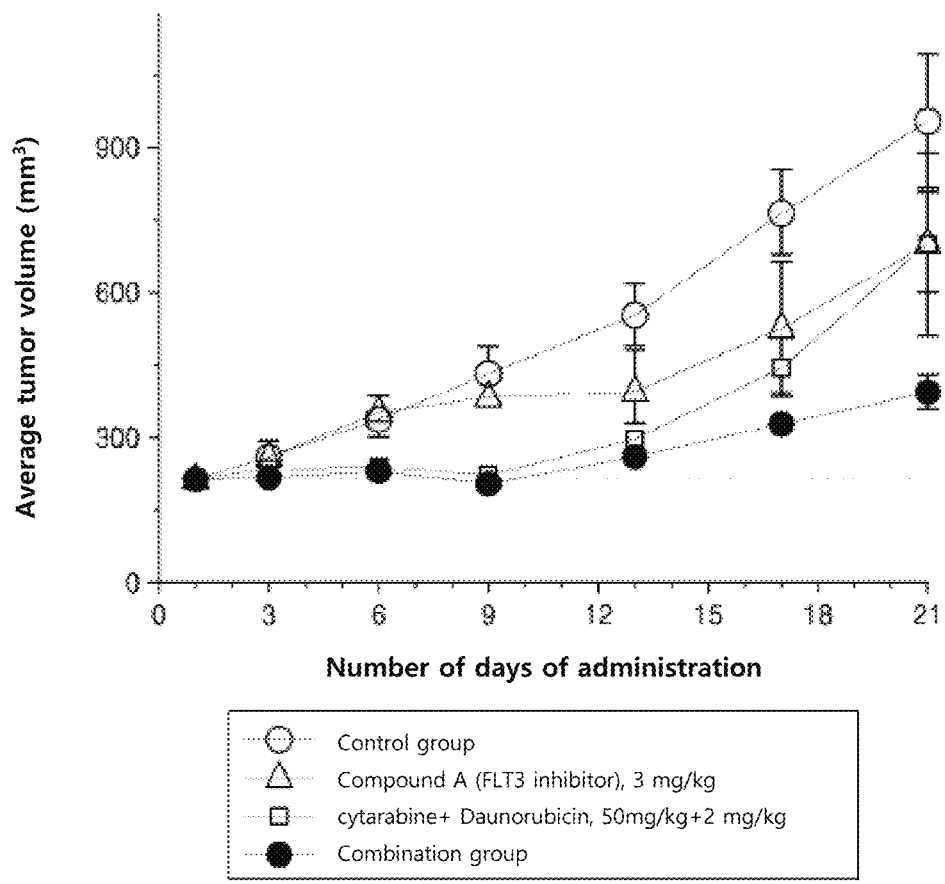

PHARMACEUTICAL COMPOSITION FOR TREATING ACUTE MYELOID LEUKEMIA, CONTAINING FLT3 INHIBITOR AND CHEMOTHERAPEUTIC AGENTS

CROSS-REFERENCE TO RELATED APPLICATIONS

This application is a U.S. National Stage Application under 35 U.S.C. § 371 of International Application No. PCT/KR2020/008258, filed Jun. 25, 2020, which claims priority to and the benefit of Korean Patent Application No. 10-2019-0077302, filed Jun. 27, 2019, the disclosure of each of which are hereby incorporated by reference in its entirety for all purposes.

TECHNICAL FIELD

The present invention relates to a pharmaceutical composition for treating acute myeloid leukemia, containing an effective treatment composition of Fms-Like Tyrosine kinase-3 (FLT3) inhibitor and chemotherapeutic agents; and a method of treatment using such composition.

BACKGROUND ART

Fms-Like Tyrosine kinase-3 (FLT3) is one of the most frequently mutated genes in acute myeloid leukemia (AML). Mutant FLT3 (Mutant FLT3) refers to a mutation expressed in leukemia cells that appears in a subpopulation of acute myeloid leukemia (AML) patients. Activating mutations in FLT3, such as intragene tandem duplication (ITD) in the proximal domain, appear in about 25-30% of newly diagnosed AML cases (Patent Document 1). It is known that FLT3 mutation occurs in about ⅓ of acute myeloid leukemia (AML) patients (Non-Patent Document 1).

While several FLT3 inhibitors are available clinically, drug-resistant leukocytes have been observed in AML patients treated with these FLT3 inhibitors, and drug resistance was indicated (Non-Patent Document 1). Further, with conventional acute myeloid leukemia (AML) standard chemotherapy, targeting to AML stem/progenitor cells is impossible, so the disease frequently recurs in patients, and accordingly, there is a problem in that long-term efficacy is limited (Non-Patent Document 2). AML patients with FLT3-ITD mutations treated with Cytarabine (AraC) and anthracycline (such as daunorubicin (DNR) or idarubicin (IDR)) alone or in combination chemotherapy also exhibit a poor prognosis (Non-Patent Document 4). Thus, there is a need for a method that can solve drug resistance caused by mutations with tyrosine kinase and effectively treat patients with mutant acute leukemia.

As an attempt to address resistance to FLT3 inhibitors, inhibitors of the PI3K/Akt, MAPK, and JAK/STAT signaling pathways, as well as FLT3 inhibitors following the concomitant use of various FLT3 inhibitors and chemotherapeutic agents, were studied (Non-Patent Documents 3, 4, 5).

Chemotherapeutic agents refer to drugs used in chemotherapy, and include Cytarabine (AraC), daunorubicin (DNR), idarubicin (IDR), doxorubicin, and the like. For example, cytarabine is a drug referred to as "4-amino-1-[(2R,3S,4S,5R)-3,4-dihydroxy-5-(hydroxymethyl)oxolan-2-yl]pyrimidin-2-one", it is clinically used for acute myeloid leukemia, acute lymphocytic leukemia, chronic myelogenous leukemia, and non-Hodgkin's lymphoma, daunorubicin is a drug referred to by the chemical name of "((8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione", it is clinically used for acute myeloid leukemia, acute lymphocytic leukemia, chronic myelogenous leukemia, and Kaposi's sarcoma. Idarubicin is a drug referred to by the chemical name of "(1S,3S)-3-Acetyl-3,5,12-trihydroxy-6,11-dioxo-1,2,3,4,6,11-hexahydrotetracene-1-yl 3-Amino-2,3,6-trideoxo-α-L-ilso-hexopyranoside"; it is marketed under the trade name Zavedos. Doxorubicin is a drug referred to by the chemical name of "(7S,9S)-7-[(2R,4S,5S,6S)-4-amino-5-hydroxy-6-methyloxane-2-yl]oxy-6,9,11-trihydroxy-9-(2-hydroxy-acetyl)-4-methoxy-8,10-dihydro-7H-tetracene-5,12-dione", it is marketed under the trade name of Adriamycin, and is clinically used for breast cancer, bladder cancer, acute lymphocytic leukemia, and the like. Gilteritinib is a drug referred to by the chemical name of "6-ethyl-3-({3-methoxy-4-[4-(4-methylpiperazine-1-yl)piperidine-1-yl]phenyl}amino)-5-(tetrahydro-2H-pyran-4-ylamino)pyrazine-2-carboxamide", it is marketed under the trade name Xospata and may exist, for example, as a hemifumarate salt. Non-Patent Document 4 proposes an effective combination of gilteritinib or a salt thereof and chemotherapeutic agents or a salt thereof for treating acute myeloid leukemia (AML).

PRIOR ART DOCUMENT

Patent Document

[Patent Document 1] Korean Unexamined Patent Application Publication No. 10-2018-0124055

Non-Patent Documents

[Non-Patent Document 1] Mol Cancer Ther 2007; 6(7). July 2007
[Non-Patent Document 2] J Natl Cancer Inst. Vol. 106, Issue 2, djt440, Feb. 5, 2014
[Non-Patent Document 3] Oncogene. 2010 Sep. 16; 29(37): 5120-34
[Non-Patent Document 4] Oncotarget, 2019, Vol 10, No. 26
[Non-Patent Document 5] Blood 2016128:1071

DETAILED DESCRIPTION OF THE INVENTION

Problem to be Solved by the Invention

The present invention can lead to better therapeutic outcomes by providing an alternative therapy for the treatment of AML, including patients with FLT3 mutations.

Means for Solving the Problem

FLT3 is a promising therapeutic target for leukemia and is mutated in approximately 30% or more of AML patients. However, there is growing interest in the development of drug resistance and refractories resulting from the emergence of point mutations in targeted tyrosine kinases used for the treatment of patients with acute leukemia. One approach to overcoming this resistance is identified by combining structurally unrelated inhibitors and/or inhibitors of different signaling pathways to determine whether efficacy and therapeutic effect are enhanced.

One aspect of the present invention provides a pharmaceutical composition for the treatment of acute myeloid leukemia (AML), wherein, as a pharmaceutical composition comprising an Fms-like tyrosine kinase-3 (FLT3) inhibitor, a pharmaceutically acceptable salt thereof, or a solvate thereof, the composition is administered in combination with chemotherapeutic agents, pharmaceutically acceptable salts, or solvates thereof; in this case, the FLT3 inhibitor is a compound selected from the compound of Formula 1, stereoisomers, tautomers, and combinations thereof.

Another aspect of the present invention provides a pharmaceutical composition for the treatment of acute myeloid leukemia (AML), wherein as a pharmaceutical composition comprising a chemotherapeutic agent, or a pharmaceutically acceptable salt or solvate thereof, it is administered in combination with an Fms-like tyrosine kinase (FLT3) inhibitor, or a pharmaceutically acceptable salt or solvate thereof.

Yet another aspect of the present invention provides a pharmaceutical combination for the treatment of acute myeloid leukemia (AML), comprising a FLT3 inhibitor, a pharmaceutically acceptable salt or solvate thereof, and a chemotherapeutic agent, a pharmaceutically acceptable salt or solvate thereof; in this case, the FLT3 inhibitor is a compound selected from the compound of Formula 1, stereoisomers, tautomers, and combinations thereof, Another aspect of the present invention provides a pharmaceutical kit comprising instructions for administering the pharmaceutical composition or pharmaceutical combination simultaneously, sequentially or separately.

Another aspect of the present invention provides a treatment method for treating acute myeloid leukemia (AML) using the pharmaceutical composition, pharmaceutical combination, or kit.

Effects of the Invention

One aspect of the present invention provides a pharmaceutical composition tor treating acute myeloid leukemia (AML), comprising a therapeutically effective combination of an ms-like tyrosine kinase inhibitor, a chemotherapeutic agent, or a pharmaceutically acceptable salt thereof, or a solvate thereof.

Another aspect of the present invention provides a method of treating acute myeloid leukemia (AML) using the pharmaceutical composition; and the above pharmaceutical composition, pharmaceutical combinations and kit using the same for treating acute myeloid leukemia.

By providing the pharmaceutical composition, pharmaceutical combination, methods of treatment, and kit, the effectiveness of treatment for AML in subjects with acute myeloid leukemia (AML), including individuals with FLT3 mutations present, may be enhanced.

BRIEF DESCRIPTION OF THE DRAWINGS

The FIGURE shows the results of measuring the average tumor volume following administration of Cytarabine (AraC) or anthracycline (eg, daunorubicin (DNR)), constituting 5-chloro-N-(3-cyclopropyl-5-(((3R,5S)-3,5-dimethylpiperazin-1-yl)methyl)phenyl)-4-(6-methyl-1H-indole-3-yl)pyrimidin-2-amine and chemotherapeutic agents that are FLT3 inhibitors in nude mice xenografted with MV-4-11 cell line, alone or in combination. The Y-axis represents the average tumor volume, and the X-axis represents the number of dosing days.

FORM FOR CARRYING OUT THE INVENTION

All technical terms used in the present invention, unless otherwise defined, have the same meaning as commonly understood by one of ordinary skill in the art of the present invention. In addition, although preferred methods and samples are described herein, similar or equivalent ones are also included in the scope of the present invention. In addition, the numerical value described in this specification is considered to include the meaning of "about" even if not specified. The details of all publications incorporated herein by reference are hereby incorporated by reference in their entirety.

One aspect of the present invention provides a pharmaceutical composition, combination, kit, or method for treating AML using the same for the treatment of acute myeloid leukemia (AML), comprising in a combination effective for the treatment of acute myeloid leukemia, an Fms-like tyrosine kinase (FLT3) inhibitor, or any pharmaceutically acceptable salt thereof, or a solvate thereof, and a chemotherapeutic agent, or any pharmaceutically acceptable salt thereof, or a solvate thereof.

In the present specification, acute myeloid leukemia (AML) is a disease in which hematopoietic stem cells turn into malignant cells, proliferate in the bone marrow, spread to the peripheral blood and spread throughout the body, invading the liver, spleen, lymph glands, etc.; it may comprise acute myeloid leukemia with FLT3 mutations. In one embodiment, the acute myeloid leukemia may include a mutant FLT3 polynucleotide-positive myeloid leukemia, a longitudinal duplication (ITD) positive acute myeloid leukemia in the FLT3 gene, or an acute myeloid leukemia having a FLT3 point mutation.

As used herein, Fms-Like Tyrosine kinase-3: (FLT3) is a member of the class III receptor tyrosine kinase (TK) family that is normally expressed on the surface of hematopoietic stem cells. FLT3 and its ligands play important roles in proliferation, survival and differentiation of pluripotent stem cells. FLT3 is expressed in many AML cases. Further, Tyrosine kinase domain (TKD) mutations near D835 in activated FLT3 and activation loops with intragenic longitudinal duplication (ITD) in and around the proximal domain are present in 28% to 34% and 11% to 14% of AML cases, respectively. These activating mutations in FLT3 are tumorigenic, and exhibit transforming activity in cells. Patients with FLT3-ITD mutations have a poor prognosis in clinical studies, a higher rate of recurrence, a shorter duration of remission from initial treatment (6 months versus 11.5 months in patients without FLT3-ITD mutation), decreased disease-free survival (16% to 27% versus 41% at 5 years), and reduced OS (15% to 31% versus 42% at 5 years). The incidence of recurrence after hematopoietic stem cell transplantation (HSCT) is also higher for patients with FLT3-ITD (30% versus 16% of patients without the FLT3-ITD mutation at 2 years). Similar to the prognosis for first-line treatment, patients with relapsed/refractory FLT3-mutant-positive AML have a lower rate of remission by salvage chemotherapy, the remission period to secondary relapse is shorter, and there is a reduced OS for FLT3-mutant-negative patients.

In the present specification, the FLT3 inhibitor comprises a substance such as 4'-N-benzoylstaurosporin (ingredient name: midostaurin); 6-ethyl-3-[[3-methoxy-4-[4-(4-methyl-1-piperazinyl)-1-piperidinyl]phenyl]amino]-5-[(tetrahydro-2H-pyran-4-yl)amino]-2-pyrazinecarboxamide (ingredient name: Gilteritinib); 1-(2-{5-[(3-methyloxetane-3-yl)methoxy]-1H-benzimidazol-1-yl}quinoline-8-yl)piperidine-4-amine (Ingredient Name: Crenolanib); 1-(5-(tert-butyl)isoxazol-3-yl)-3-(4-(7-(2-morpholinoethoxy)benzo[d]imidazo[2,1-b]thiazole-2-yl)phenyl)urea (ingredient name: Quizartinib); 2-hydroxy-1-(2-((9-((1r,4r)-4-methylcyclohexyl)-9H-pyrido[4',3':4,5]pyrrolo[2,3-d]pyrimidin-2-yl)

amino)-7,8-dihydro-1,6-naphthyridine-6(5H)-yl)ethanone (development code name: FLX925); (S,E)-N-(1-((5-(2-((4-cyanophenyl)amino)-4-(propylamino)pyrimidin-5-yl)pent-4-yn-1-yl)amino)-1-oxopropan-2-yl)-4-(dimethylamino)-N-methylbut-2-ynamide (development code name: FF-10101); and 6-[[(1R,2S)-2-aminocyclohexyl]amino]-7-fluoro-4-(1-methylpyrazol-4-yl)-1,2-ddihydropyrrolo[3, 4-c]pyridine-3-one (development code name: TAK-659); a compound having kinase inhibitory activity described in International Patent Application Publication No. WO2018-139903; or a compound having FLT3 inhibitory activity described in Korean Patent Application No. 10-2018-0086768 (Registration No. 10-1954370); or inhibitors in the form of any pharmaceutically acceptable salt or solvate thereof, such as a hydrate, but is not limited to these substances.

The FLT3 inhibitor may be a compound having the kinase inhibitory activity described in International Patent Application Publication No. WO2018-139903; a compound having the FLT3 inhibitory activity described in Korea Patent Application No. 10-2018-0086768 (Registration No. 10-1954370); or inhibitors in the form of any pharmaceutically acceptable salt or solvate thereof, such as a hydrate, but is not limited to these substances.

As an FLT3 inhibitor, the compound having kinase inhibitory activity described in International Patent Application Publication No. WO2018-139903 may be a compound selected from the compounds of Formula 1 described herein, stereoisomers, tautomers, and combinations thereof.

As an FLT3 inhibitor, the compound having FLT3 inhibitory activity described in the Korean Patent Application No. 10-2018-0086768 (registration number 10-1954370) may be a compound selected from the compounds of Formula 3 described herein, stereoisomers, tautomers, and combinations thereof.

One aspect of the present invention provides a pharmaceutical composition for the treatment of acute myeloid leukemia (AML), wherein as a pharmaceutical composition comprising an Fms-like tyrosine kinase-3 (FLT3) inhibitor, a
pharmaceutically acceptable salt thereof, or a solvate thereof, the composition is administered in combination with chemotherapeutic agents, pharmaceutically acceptable salts, or solvates thereof;
in this case, the FLT3 inhibitor is a compound selected from the compound of Formula 1, stereoisomers, tautomers, and combinations thereof,

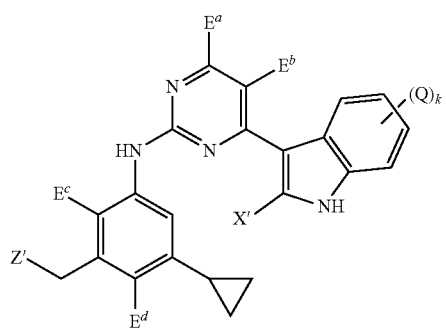

[Formula 1]

in Formula 1,
$E^a$ is hydrogen, hydroxy or $C_{1-4}$ alkoxy,
$E^b$ is hydrogen, halogen, $C_{1-4}$ alkyl or $C_{1-4}$ fluoroalkyl;
$E^c$ and $E^d$ are independently of each other hydrogen or hydroxy;
X' is hydrogen or hydroxy;
k is an integer from 1 to 2;
each Q is independently of the other hydroxy, halogen, $C_{1-4}$ alkyl, hydroxy$C_{1-4}$ alkyl or $C_{1-4}$ alkoxy;
Z' is a monovalent functional group shown in formula (2);

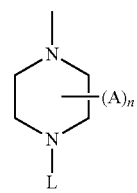

[Formula 2]

in this case, in Formula 2, n is an integer of 1 to 2;
each A is, independently of the other, a functional group selected from hydroxy, $C_{1-4}$ alkyl and hydroxy$C_{1-4}$ alkyl, wherein at least one A is $C_{1-4}$ alkyl; and
L is hydrogen, $C_{1-4}$ alkyl, hydroxy or hydroxy $C_{1-4}$ alkyl.

As used herein, the term "solvate" refers to a molecular complex of a compound of the present invention (or a pharmaceutically acceptable salt thereof) with one or more solvent molecules. Such solvent molecules may be those known or commonly used in the pharmaceutical art, for example, water, ethanol, and the like. The term "solvate" includes hydrates. The term "hydrate" refers to a complex in which the solvent molecule is water.

As used herein, the term "salt" or "pharmaceutically acceptable salt" refers to a pharmaceutically acceptable derivative of a disclosed compound, wherein the parent compound is denatured by converting an existing acid or base moiety to its salt form.

In one embodiment, the FLT3 inhibitor may be a compound selected from the compound of Formula 3, stereoisomers, tautomers, and combinations thereof.

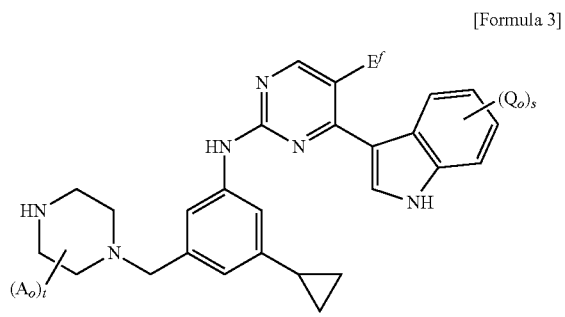

[Formula 3]

in Formula 3,
$E^f$ is fluorine, chlorine, bromine or iodine;
$Q_o$ is hydroxy, halogen, C 1-4 alkyl, hydroxyC 1-4 alkyl or C 1-4 alkoxy;
s is an integer from 1 to 2;
$A_o$ is a functional group selected from hydroxy, C 1-4 alkyl and hydroxyC 1-4 alkyl; and
t is an integer from 1 to 2.
For example, the FLT3 inhibitor may be a compound having kinase inhibitory activity described in International Patent Application Publication No. WO2018-139903; for example, it may be a compound selected from the group consisting of compounds listed in Nos. 1 to 55 of Table 1, any pharmaceutically acceptable salts thereof, and solvates including hydrates.

TABLE 1

| Number | Compound Name |
|---|---|
| 1 | 2-(4-(3-((5-chloro-4-(6-fluoro-1H-indol-3-yl)pyrimidin-2-yl)amino)-5-cyclopropylphenine)piperazine-1-in)ethane-1-ol |
| 2 | 2-(4-(3-((5-chloro-4-(6-methyl-1H-in-3yl)pyrimidin-2yl)amino)-5-cyclopropylphenine)piperazine-1-yl) ethane-1-ol |
| 3 | 5-chloro-N-(3-cyclopropyne-5-(4-(dimethylamino) piperidine-1-yl-) phenyl)-4-(IH-indol-3-yl) pyrimidin-2-amine |
| 4 | (S)-1-((1-(3-((5-chloro-4-(1H-indol-3-yl)pyrimidin-2-yl)amino)-5-cyclopropylphenyl)piperidine-4-yl) (methyl) amino) propan-2-ol |
| 5 | (S)-1-((1-(3-((5-chloro-4-(6methyl-1H-indol-3-yl)pyrimidin-2-yl)amino)-5-cyclopropylphenyl) piperidine-4-yl) (methyl) amino) propan-2-ol |
| 6 | 5-chloro-N-(3-cyclopropyl-5-(4-(dimethylamino)piperidine-1-yne)phenyl)-4-(6-methyl-1H-indol-3-yl)pyrimidin-2-amine |
| 7 | 2-(4-(3-((5-chloro-4-(6-methoxy-1H-indol-3-yl)pyrimidin-2-yl)amino)-5-cyclopropylphenyl)piperazine-1-yl) ethanol-1-ol |
| 8 | (S)-1-(1-3-((5-chloro-4-(1H-indol-3-yl)pyrimidin-2-yl)amino)-5-cyclopropylphenyl)piperidine-4-yl-) pyrrolidine-3-ol |
| 9 | (S)-1-(1-(3-((5-chloro-4-(6-methyl-1H-indol-3-yl)pyrimidin-2-yl)amino)-5-cyclopropylphenyl) piperidine-4-yl)pyrrolidine-3-ol |
| 10 | 5-chloro-N-(3-cyclopropyl-5-(4-(dimethylamino) piperidine-1-yl) phenyl)-4-(6-metoxy-1H-indol-3-yl) pyrimidine-2-amine |
| 11 | (S)-1-(1-(3-((5-chloro-4-(6-methoxy-1H-indol-3-yl)pyrimidin-2-yl)amino)-5-cyclopropylphenyl-) piperidine-4-yl-) pyrrolidine-3-ol |
| 12 | 2-(4-(3-(4-(1H-Indol-3-yl)-5-methylpyrimidin-2-yl)amino)-5-cyclopropylphenyl)piperazine-1-yl)ethane-1-ol |
| 13 | 5-chloro-N-(3-cyclopropyl-5-(4-morpholinopiperidine-1-yne)phenyl)-4-(6-methyl-1H-indol-3-yl)pyrimidin-2-amine |
| 14 | 5-chloro-N-(3-cyclopropyl-5-(4-(ethyl (methyl) amino) piperidine-1-yl) phenyl)-4-(6-methyl-1H-indole-3-yl) pyrimidin-2-amine |
| 15 | 5-chloro-N-(3-cyclopropyl-5-(4-(diethylamino) piperidine-1-yl-)phenyl)-4-(6-methyl-1H-indol-3-yl) pyrimidin-2-amine |
| 16 | 5-chloro-N-(3-cyclopropyl-5-(3-(dimethylamino) pyrrolidine-1-yl-) phenyl)-4-(6-methyl-1H-indol-3-yl) pyrimidin-2-amine |
| 17 | 2-(4-(3-((5-chloro-4-(6-methyl-1H-indol-3-yl)pyrimidin-2-yl)amino)-5-cyclopropylphenyl)piperazine-1-yl)-2-methylpropan-1-ol |
| 18 | N-(3-(4-aminopiperidine-1-yl)-5-cyclopropylphenyl)-5-chloro-4-(6-methyl-1H-indol-3-yl)pyrimidin-2-amine |
| 19 | 5-chloro-N-(3-cyclopropyl-5-(4-(methylamino) piperidine-1-yl) phenyl)-4-(6-methyl-1H-indol-3-yl) pyrimidin-2-amine |
| 20 | 2-(4-(3-((5-chloro-4-(6-fluoro-1H-indol-3-yl)pyrimidin-2-yl)amino)-5-cyclopropylphenyl)piperazine-1-yl)-2-methylpropan-1-ol |
| 21 | 2-(4-(3-((5-chloro-(6-methyl-1H-indol-3yl)pyrimidin-2-yl)amino)_5cyclopropylphenyl)piperidine-1-yl) ethane-1-ol |
| 22 | 2-(4-(3-((5-chloro-4-(6-chloro1H-indol-3-yl)pyrimidin-2-yl)amino)-5-cyclopropylphenyl)pyrimizine-1-yl) ethanol-1-ol |
| 23 | 5-chloro-N-(3-cyclopropyl-5-(4-(pyrrolidin-1-yl)piperidine-1-yl)phenyl)-4-(6-methyl-1H-indole-3-yl) pyrimidin-2-amine |
| 24 | 1-(1-(3-((5-chloro-4-(6-methyl-1H-indol-3-yl) pyrimidin-2-yl-) amino)-5-cyclopropylphenyl-) piperidine-4-in)azetidine-3-ol |
| 25 | 2-(4-(3-((5-chloro-4-(-1H-indol-3-yl)pyrimidin-2-yne)amino)-5-methoxyphenyl)piperazine-1-yl)ethane-1-ol |
| 26 | 2-(4-(3-((5-chloro-4-(6-fluoro-IH-indol-3-yl)pyrimidin-2-yl)amino)phenyl)piperidine-1-yl)ethane-1-ol |
| 27 | 2-(4-(3-((5-chloro-4-(IH-indol-3-yl)piperidine-2yl)amino)phenyl)piperidine-1-yl)ethane-1-ol |
| 28 | 2-(4-(3-((5-chloro-4-(IH-indol-3-yl)pyrimidin-2-yl)amino)phenyl)piperazine-1-ynyl)ethane-1-ol |
| 29 | 5-chloro-N-(3-(4-(dimethylamino) pyrimidin-1-yl-) phenyl)-4-(IH-indol-3-yl) pyrimidin-2-amine |
| 30 | 5-chloro-N--(3-(3-(dimethylamino)pyrimidin-1-yl)phenyl)-4-(IH-indol-3-yl)pyrimidin-2-amine |
| 31 | 2-(4-(3-((5-chloro-4-(6-fluoro-1H-indol-3-yl)pyrimidin-2-yl)amino)phenyl)piperidine-1-yl)ethane-1-ol |
| 32 | 2-(4-(3-((5-chloro-4-(6-fluoro-1H-indol-3-yl)pyrimidin-2-yl)amino)-5-methoxyphenyl)piperazine-1-yl) ethanol-1-ol |
| 33 | 2-(4-(3-(5-chloro-4-(1H-indol-3-yl)pyrimidin-2-yl)amino)-5-isopropoxyphenyl)piperazine-1-yl)ethane-1-ol |
| 34 | 5-chloro-N-(3-cyclopropyl-5-(piperazin-1-ylmethyl) phenyl)-4-(6-fluoro-1H-indol-3-yl) pyrimidin-2-amine |
| 35 | 2-(4-(3-((5-chloro-4-(-6-fluoro-1H-indol-3-yl)pyrimidin-2-yl)amino)-5-methoxybenzyl)piperazine-1-yl) ethane-1-ol |
| 36 | 2-(4-(3-((5-chloro-4-(6-fluoro-1H-indol-3-yl)pyrimidin-2-yl)amino)benzyl)piperazine-1-yl)ethane-1-ol |

TABLE 1-continued

| Number | Compound Name |
|---|---|
| 37 | 2-(4-(3-((5-chloro-1H-indol-3-yl)pyrimidin-2-yl)amino)-5-methoxybenzyl)piperazine-1-yl)ethane-1-ol |
| 38 | 2-(4-(3-((5-chloro-4-(1H-indol-3-yl)pyrimidin-2-yl)amino)-5-cyclopropylbenzyl)piperazine-1-yl)-2-methylpropan-1-ol |
| 39 | (S)-1-((1-3-((5-chloro-4-(1H-indol-3-yl)pyrimidin-2-yl)amino)-5-cyclopropylbenzyl)piperidine-4-yl) (methyl) amino) propan-2-ol |
| 40 | (S)-1-((1-3-((5-chloro-4-(6-methyl-1H-indol-3-yl)pyrimidin-2-yl)amino)-5-cyclopropylbenzyl) piperidine-4-yl) (methyl) amino) propan-2-ol |
| 41 | 2-(4-(3-((5-chloro-4-(6-methyl-1H-indol-3-yl)pyrimidin-2-yl)amino)-5-cyclopropylbenzyl)piperazine-1-yl)-2-methylpropan-1-ol |
| 42 | (S)-1-((1-3-((5-chloro-4-(1H-indol-3-yl)pyrimidin-2-yl)amino)-5-cyclopropylbenzine)piperidine-4-yl) pyrrolidine-3-ol |
| 43 | (S)-1-((1-3-((5-chloro-4-(6-methyne-1H-indol-3-yl)pyrimidin-2-yl)amino)-5-cylanropropylbenzyl-)piperidine-4-yl)pyrrolidine-3-ol |
| 44 | (S)-1-((1-3-((5-chloro-4-(6-methoxy-1H-indol-3-yl)pyrimidin-2-yl)amino)-5-cyclopropylbenzyl) piperidine-4-yl)pyrrolidine-3-ol |
| 45 | 1-(3-((5-chloro-4-(6-methyl-1H-indol-3-yl) pyrimidin-2-yl) amino)-5-cyclopropylbenzyl) piperidine-4-ol |
| 46 | (S)-5-chloro-N-(3-cyclopropyl-5-((3-(dimethylamino)pipolydine-1-yl)methyl)phenyl)-4-(6-methyl-1H-indole-3-yl)pyrimidin-2-amine |
| 47 | 1-(4-)3-((5-chloro-4-(6-fluoro-1H-indol-3-yl)pyrimidin-2-yl)amino)-5-cyclopropylbenzyl)piperazine-1-yl)-2-hydroxyethan-1-one |
| 48 | 1-(4-(3-( (5-chloro-4-(6-methyl-1H-indol-3-yl) pyrimidin-2-yl-) amino)-5-cyclopropylbenzyl) piperazine-1-yl)-2-hydroxyethan-1-one |
| 49 | 2-(4-(3-((5-chloro-4-(6-ethyl-1H-indol-3-yl)pyrimidin-2-yl)amino)-5-cyclopropylbenzyl)piperazine-1-yl) ethan-1-ol |
| 50 | (3-((5-chloro-4-(1H-indol-3-yl)pyrimidin-2-yl)amino)-5-methoxy phenyl)(4-(2-hydroxyethyl)piperazine-1-yl) methanone |
| 51 | 1-(2-(3-((5-chloro-4-(6-methyl-1H-indol-3-yl)pyrimidin-2-yl)amino)-5-cyclopropylphenoxy)ethyl)piperidine-4-ol |
| 52 | 1-(2-(3-((5-chloro-4-(6-methyl-1H-indol-3-yl) pyrimidin-2-yl) amino-5-ethylphenoxy)ethyl) piperidine-4-ol |
| 53 | (R)-2-(3-(3-((5-chloro-4-(6-methyl-1H-indol-3-yl)pyrimidin-2-yl)amino)-5-cyclopropylphenoxy) pyrrolidine-1-yl)ethan-1-ol |
| 54 | 2-(4-(3-((5-chloro-4-(6-methyl-1H-indol-3-yl)pyrimidin-2-yl)amino)-5-cyclopropylphenoxy)piperidine-1-yl-) ethan-1-ol |
| 55 | 2-(4-(3-((5-chloro-4-(1H-indol-3-yl)pyrimidin-2-yl)amino)-5-methoxyphenoxy)piperidine-1-yl)ethane-1-ol |

For example, the FLT3 inhibitor may be a compound having FLT3 inhibitory activity described in Korean Patent Application No. 10-2018-0086768; for example, it may be a compound selected from the group consisting of compounds listed in Nos. 1 to 32 of Table 2, any pharmaceutically acceptable salts thereof, and solvates including hydrates.

TABLE 2

| No. | Name of Compound |
|---|---|
| 1 | 5-chloro-N-(3-cyclopropyl-5-(((3R,5S)-3,5-dimethylpiperazine-1-yl)methyl)phenyl)-4-(6-fluoro-1H-indol-3-yl)pyrimidine-2-amine |
| 2 | 5-chloro-5-(6-chloro-1H-indol-3-yl)-N-(3-cyclopropyl-5-(((3R,5S)-3,5-dimethylpiperazine-1-yl)methyl)phenyl)pyrimidine-2-amine |
| 3 | 2-((2R,6S)-4-(3-((5-chloro-4-(6-fluoro-1H-indol-3-yl)pyrimidine-2-yl)amino)-5-cyclopropylbenzyl)-2,6-dimethylpiperazine-1-yl)ethan-1-ol |
| 4 | 2-((2R,6S)-4-(3-((5-chloro-4-(1H-indol-3-yl)pyrimidine-2-yl)amino)-5-cyclopropylbenzyl)-2,6-dimethylpiperazine-1-yl)ethan-1-ol |
| 5 | 2-((2R,6S)-4-(3-((5-chloro-4-(6-methyl-1H-indol-3-yl)-pyrimidine-2-yl)amino)-5-cyclopropylbenzyl)-2,6-dimethylpiperazine-1-yl)ethan-1-ol |
| 6 | (R)-5-chloro-N-(3-cyclopropyl-5-((3-methylpiperazine-1-yl)methyl)phenyl)-4-(1H-indol-3-yl)-pyrimidine-2-amine |
| 7 | (R)-5-chloro-N-(3-cyclopropyl-5-((3-methylpiperazine-1-yl)methyl)phenyl)-4-(6-methyl-1H-indol-3-yl)pyrimidine-2-amine |
| 8 | 5-chloro-N-(3-cyclopropyl-5-(((3R,5S)-3,5-dimethylpiperazine-1-yl)methyl)phenyl)-4-(6-methyl-1H-indol-3-yl)pyrimidine-2-amine |
| 9 | 5-chloro-N-(3-cyclopropyl-5(((3S,5R)-3-ethyl-5-methylpiperazine-1-yl)methyl)phenyl)-4-(6-methyl-1H-indol-3-yl)pyrimidine-2-amine |
| 10 | 5-chloro-N-(3-cyclopropyl-5-((3,5-dimethylpiperazine-1-yl)methyl)phenyl)-4-(6-methyl-1H-indol-3-yl)pyrimidine-2-amine |
| 11 | N-(3-cyclopropyl-5-(((3R,5S)-3,5-dimethylpiperazine-1-yl)methyl)phenyl)-5-fluoro-4-(6-methyl-1H-indol-3-yl)pyrimidine-2-amine |
| 12 | N-(3-cyclopropyl-5-(((3R,5S)-3,5-dimethylpiperazine-1-yl)methyl)phenyl)-5-fluoro-4-(6-methyl-1H-indol-3-yl)pyrimidine-2-amine |
| 13 | N-(3-cyclopropyl-5-(((3R,5S)-3,5-dimethylpiperazine-1-yl)methyl)phenyl)-4-(1H-indol-3-yl)-5-methylpyrimidine-2-amine |

TABLE 2-continued

| No. | Name of Compound |
|---|---|
| 14 | N-(3-cyclopropyl-5-(((3R,5S)-3,5-dimethylpiperazine-1-yl)methyl)phenyl)-5-methyl-4-(6-methyl-1H-indol-3-yl)pyrimidine-2-amine |
| 15 | N-(3-cyclopropyl-5-(((3R,5S)-3,5-dimethylpiperazine-1-yl)methyl)phenyl)-4-(6-methyl-1H-indol-3-yl)-5-(trifluoromethyl)pyrimidine-2-amine |
| 16 | (3-(5-chloro-2-((3-cyclopropyl-5-(((3R,5S)-3,5-dimethylpiperazine-1-yl)methyl)phenyl)amino)pyrimidine-4-yl)-1H-indol-6-yl)methanol |
| 17 | 5-chloro-N-(3-cyclopropyl-5-(((3R,5S)-3,5-dimethylpiperazine-1-yl)methyl)phenyl)-4-(5-methoxy-6-methyl-1H-indol-3-yl)pyrimidine-2-amine |
| 18 | 3-(5-chloro-4-((3-cyclopropyl-5-(((3R,5S)-3,5-dimethylpiperazine-1-yl)methyl)phenyl)amino)pyrimidine-4-yl)-6-methyl-1H-indol-5-ol |
| 19 | 3-(5-chloro-2-((3-cyclopropyl-5-(((3R,5S)-3,5-dimethylpiperazine-1-yl)methyl)phenyl)amino)pyrimidine-4-yl)-6-methylindoline-2-on |
| 20 | 5-chloro-N-(3-cyclopropyl-5-(((3R,5S)-3,5-dimethylpiperazine-1-yl)methyl)phenyl)-4-methoxy-6-(6-methyl-1H-indol-3-yl)pyrimidine-2-amine |
| 21 | 5-chloro-2-((3-cyclopropyl-5-(((3R,5S)-3,5-dimethylpiperazine-1-yl)methyl)pneny1)amino)-6-(6-methyl-1H-indol-3-yl)pyrimidine-4-ol |
| 22 | 3-(5-chloro-2-((3-cyclopropyl-5-(((3R,5S)-3,5-dimethylpiperazine-1-yl)methyl)phenyl)amino)pyrimidine-4-yl)-6-methyl)-1H-indol-7-ol |
| 23 | 2-((5-chloro-4-(6-methyl-1H-indol-3-yl)pyrimidine-2-yl)amino)-4-cyclopropyl-6-(((3R,5S)-3,5-dimethylpiperazine-1-yl)methyl)phenol |
| 24 | 4-((5-chloro-4-(6-methyl-1H-indol-3-yl)pyrimidine-2-yl)amino)-2-cyclopropyl-6-(((3R,5S)-3,5-dimethylpiperazine-1-yl)methyl)phenol |
| 25 | (R)-5-chloro-N-(3-cyclopropyl-5-((3,3,5-trimethylpiperazine-1-yl)methyl)phenyl)-4-(6-methyl-1H-indol-3-yl)pyrimidine-2-amine |
| 26 | ((2R,6R)-4-(3-((5-chloro-4-(6-methyl-1H-indol-3-yl)pyrimidine-2-yl)amino)-5-cyclopropylbenzyl)-6-methylpiperazine-2-yl)methanol |
| 27 | (R)-5-chloro-N-(3-cyclopropyl-5-((5-methyl-4H-diazaspiro[2,5]octan-7-yl)methyl)phenyl)-4-(6-methyl-1H-indol-3-yl)pyrimidine-2-amine |
| 28 | 5-chloro-N-(3-cyclopropyl-5-(((3R,5R)-3,5-dimethylpiperazine-1-yl)methyl)phenyl)-4-(6-methyl)-1H-indol-3yl)-pyrimidine-2-amine |
| 29 | 5-chloro-N-(3-cyclopropyl-5-(((3S,5S)-3,5-dimethylpiperazine-1-yl)methyl)phenyl)-4-(6-methyl-1H-indol-3-yl)pyrimidine-2-amine |
| 30 | 5-chloro-N-(3-cyclopropyl-5-(((3R,5S)-3 4,5-trimethylpiperazine-1-yl)methyl)phenyl)-4-(6-methyl-1H-indol-3-yl)pyrimidine-2-amine |
| 31 | (2R,6S)-4-(3-((5-chloro-4-(6-methyl-1H-indol-3-yl)pyrimidine-2-yl)amino)-5-cyclopropylbenzyl)-2,6-dimethylpiperazine-1-ol |
| 32 | (2R,6S)-4-(3-cyclopropyl-5-((4-(6-methyl-1H-indol-3-yl)-pyrimidine-2-yl)amino)benzyl)-2,6-dimethylpiperazine-1-ol |

In one embodiment, the FLT3 inhibitor may be any one selected from the group consisting of the compounds shown in Table 2 above.

In one embodiment, the FLT3 inhibitor may be 5-chloro-N-(3-cyclopropyl-5-(((3R,5S)-3,5-dimethylpiperazine-1-yl)methyl)phenyl)-4-(6-methyl-1H-indole-3-yl) pyrimidin-2-amine; or it may be a pharmaceutically acceptable salt thereof, or a hydrate thereof.

As the FLT3 inhibitor, 5-chloro-N-(3-cyclopropyl-5-(((3R,5S)-3,5-dimethylpiperazine-1-yl)methyl)phenyl)-4-(6-methyl-1H-indol-3-yl)pyrimidin-2-amine inhibits kinases such as SYK, which are known to be associated with AML resistance. Among them, SYK kinase transcribes FLT3 by direct physical interaction; it is important for the development of FLT3-ITD-induced myelodysplasia and is primarily more active in FLT3-ITD-positive AML. Therefore, activation of other signaling pathways of kinases such as SYK may be responsible for resistance in the treatment of AML patients. In addition, the combination of FLT3 inhibitors and SYK inhibitors may be a more effective strategy for the treatment of AML patients.

As used herein, chemotherapeutic agents refer to drugs used in chemotherapy; they include biological (large molecule) or chemical (small molecule) compounds useful for the treatment of cancer regardless of the mechanism of action, and are also referred to as chemotherapeutic agents or antitumor agents. Such chemotherapeutic agents are well known by those skilled in the art; they may be a compound selected from the group consisting of the following substances, or any pharmaceutically acceptable salt or hydrate thereof.

Hormones and antagonists including the following: nitrogen mustards such as cyclophosphamide, ifosfamide, mechlorethamine, chlorambucil and melphalan; ethyleneamines and methylmelamines such as thiotepa; methylhydrazine derivatives such as procarbazine; alkylsulfonates such as busulfan; nitrosoureas such as carmustine or lomustine; triazenes such as dacarbazine and temozolomide; alkylating agents including platinum coordination complexes such as cisplatin, carboplatin and oxaliplatin; folic acid analogs such as methotrexate; pyrimidine analogs such as fluorouracil, cytarabine, gemcitabine and capecitabine; antimetabolites, including purine analogs such as mercaptopurine, pentostatin, cladribine and fludarabine; vinca alkaloids such as vinblastine, vinorelbine and vincristine; taxanes such as paclitaxel and docetaxel; epipodophyllotoxins such as etoposide and teniposide; camptothecins such as topotecan and irinotecan; anticancer antibiotics such as dactinomycin, daunorubicin, idarubicin, doxorubicin, plicomycin and epirubicin; anthracenediones such as mitoxantrone, mitomycin and bleomycin; mitosis inhibitors such as dolastatins; enzymes such as L-asparaginase; substituted ureas such as hydroxyurea; differentiating agents such as tretinoin; protein kinase inhibitors such as imatinib or bryostatin; proteasome inhibitors such as geftinib and bortezomib; adrenocortical suppressants such as aminoglutethimide; adrenocorticosteroids such as prednisone; progestins such as megestrol acetate and medroxyprogesterone; estrogens such as diethylstilbestrol; anti-estrogens such as tamoxifen, idoxifen, droloxifene, zindoxifene, trioxifene, ICI 182,780, EM-800 and toremifene; aromatase inhibitors such as anastrozole, letrozole and exemestane; androgens such as testosterone propionate; anti-androgens such as flutamide; and gonadotropin-releasing agents, such as leuprolide.

The chemotherapeutic agent may be one or more, such as 2, 3, 4, 5, 6 or 7 or more. For example, there may be two or more chemotherapeutic agents, for example, two chemotherapeutic agents may be used in combination.

The chemotherapeutic agent may be antimetabolites, anti-cancer antibiotics, or a combination thereof.

The antimetabolites may be a pyrimidine analog. For example, the pyrimidine analog may be fluorouracil, cytarabine, gemcitabine or capecitabine, or any pharmaceutically acceptable salt or hydrate thereof.

The anti-cancer antibiotic may be an anthracycline-based antibiotic. Anthracycline-based anticancer substances have a structural feature of having one or more deoxy sugars in an aglycone consisting of four rings. As representative anthracycline anticancer substances, daunorubicin and doxorubicin are known.

The anticancer antibiotic may be dactinomycin, daunorubicin, idarubicin, doxorubicin, plicomycin or epirubicin, or any pharmaceutically acceptable salt or hydrate thereof.

The chemotherapeutic agent includes substances such as 4-amino-1-[(2R,3S,4S,5R)-3,4-dihydroxy-5-(hydroxymethyl)oxolane-2-yl]pyrimidin-2-one (ingredient name: Cytarabine, AraC), ((8S,10S)-8-acetyl-10-[(2S,4S,5S,6S)-4-amino-5-hydroxy-6-methyl-oxane-2-yl]oxy-6,8,11-trihydroxy-1-m ethoxy-9,10-dihydro-7H-tetracene-5,12-dione (ingredient name: daunorubicin: DNR); (1S,3S)-3-acetyl-3,5,12-trihydroxy-6,11-dioxo-1,2,3,4,6,11-hexahydrotetracene-1-yl 3-amino-2,3,6-trideoxo-α-L-ilsohexopyranoside (ingredient name: idarubicin: IDR); (7S, 9S)-7-[(2R,4S,5S,6S)-4-amino-5-hydroxy-6-methyloxane-2-yl]oxy-6,9,11-trihydroxy-9-(2-hydroxyacetyl)-4-methoxy-8,10-dihydro-7H-tetracene-5,12-dione (ingredient name: doxorubicin); (8S,10S)-10-{[(2R,4S,5R,6S)-4-amino-5-hydroxy-6-methyloxane-2-yl]oxy}-6,8,11-trihydroxy-8-(2-hydroxyacetyl)-1-methoxy-5,7,8,9,10,12-hexahydrotetracene-5,12-dione (ingredient name: epirubicin); any pharmaceutically acceptable salt or hydrate form thereof, but is not limited thereto. The chemotherapeutic agent may be any one or more selected from cytarabine, daunorubicin, idarubicin, doxorubicin and epirubicin. The chemotherapeutic agent may be two or more. The chemotherapeutic agent may be a combination of cytarabine and daunorubicin.

In one embodiment, the chemotherapeutic agent may be any one or more selected from the group consisting of 4-amino-1-[(2R,3S,4S,5R)-3,4-dihydroxy-5-(hydroxymethyl)oxolane-2-yl]pyrimidin-2-one, ((8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione, pharmaceutically acceptable salts thereof, and solvates thereof.

In one embodiment, the chemotherapeutic agent may be any one or more selected from the group consisting of 4-amino-1-[(2R,3S,4S,5R)-3,4-dihydroxy-5-(hydroxymethyl)oxolan-2-yl]pyrimidin-2-one, ((8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione, pharmaceutically acceptable salts thereof, and hydrates thereof; and
the FLT3 inhibitor may be any one selected from the compound of Formula 1, stereoisomers, and tautomers thereof.

In one embodiment, the chemotherapeutic agent may be any one or more selected from the group consisting of 4-amino-1-[(2R,3S,4S,5R)-3,4-dihydroxy-5-(hydroxymethyl)oxolane-2-yl]pyrimidin-2-one; ((8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione, pharmaceutically acceptable salts thereof, and hydrates thereof; and
the FLT3 inhibitor may be any one selected from the compound of Formula 3, a stereoisomer, and a tautomer thereof.

In one embodiment, the chemotherapeutic agent may be any one or more selected from the group consisting of 4-amino-1-[(2R,3S,4S,5R)-3,4-dihydroxy-5-(hydroxymethyl)oxolane-2-yl]pyrimidin-2-one, ((8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione, pharmaceutically acceptable salts thereof, and hydrates thereof; and
the FLT3 inhibitor may be 5-chloro-N-(3-cyclopropyl-5-(((3R,5S)-3,5-dimethylpiperazine-1-yl)methyl)phenyl)-4-(6-methyl-1H-indol-3-yl)pyrimidin-2-amine.

In one embodiment, the chemotherapeutic agent may be 4-amino-1-[(2R,3S,4S,5R)-3,4-dihydroxy-5-(hydroxymethyl)oxolane-2-yl]pyrimidin-2-one, and ((8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione, or a pharmaceutically acceptable salt thereof, or a hydrate thereof; and
the FLT3 inhibitor may be any one selected from the compound of Formula 1, stereoisomers, and tautomers thereof.

In one embodiment, the chemotherapeutic agent may be 4-amino-1-[(2R,3S,4S,5R)-3,4-dihydroxy-5-(hydroxymethyl)oxolane-2-yl]pyrimidin-2-one, and ((8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione, or a pharmaceutically acceptable salt thereof, or a hydrate thereof;
the FLT3 inhibitor may be any one selected from the compound of Formula 3, a stereoisomer, and a tautomer thereof.

In one embodiment, the chemotherapeutic agent may be 4-amino-1-[(2R,3S,4S,5R)-3,4-dihydroxy-5-(hydroxymethyl)oxolan-2-yl]pyrimidin-2-one, and ((8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione.

in one embodiment, the chemotherapeutic agent may be
  4-amino-1-[(2R,3S,4S,5R)-3,4-dihydroxy-5-(hydroxymethyl)oxolane-2-yl]pyrimidin-2-one, and ((8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione;
  the FLT3 inhibitor may be any one selected from the compound of Formula 1, stereoisomers, and tautomers thereof.

In one embodiment, the chemotherapeutic agent may be 4-amino-1-[(2R,3S,4S,5R)-3,4-dihydroxy-5-(hydroxymethyl)oxolane-2-yl]pyrimidin-2-one, and ((8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione, and
  the FLT3 inhibitor may be any one selected from the compound of Formula 3, a stereoisomer, and a tautomer thereof.

In one embodiment, the chemotherapeutic agent is 4-amino-1-[(2R,3S,4S,5R)-3,4-dihydroxy-5-(hydroxymethyl)oxolane-2-yl]pyrimidin-2-one, and ((8S,10S)-8- acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione, and
the FLT3 inhibitor may be 5-chloro-N-(3-cyclopropyl-5-(((3R,5S)-3,5-dimethylpiperazine-1-yl)methyl)phenyl)-4-(6-methyl-1H-indol-3-yl)pyrimidin-2-amine.

In one embodiment, the acute myeloid leukemia may be an acute myeloid leukemia having a FLT3 mutation.

In one embodiment, the acute myeloid leukemia may be mutant FLT3 polynucleotide-positive acute myeloid leukemia, FLT3 internal tandem duplication (ITD) positive acute myeloid leukemia, or acute myeloid leukemia with a FLT3 point mutation.

In one embodiment, as a pharmaceutical composition for the treatment of acute myeloid leukemia (AML) including the FLT3 inhibitor of any one of the compound of Formula 1, or a pharmaceutically acceptable salt, or a solvate thereof,
the acute myeloid leukemia (AML) may have a mutation in a tyrosine kinase domain (TKD) (FLT3-TKD) of the FLT3 amino acid sequence.

In one embodiment, the FLT3-TKD mutation may further include an internal tandem duplication (ITD).

In one embodiment, the FLT3-TKD mutation may include any one selected from FLT3 (D835Y), FLT3 (F691L), FLT3 (F691L/D835Y), FLT3 (ITD/D835Y), FLT3 (ITD/F691L), and combinations thereof.

In the pharmaceutical composition for the treatment of acute myeloid leukemia according to one embodiment, the FLT3 inhibitor may be 5-chloro-N-(3-cyclopropyl-5-(((3R,5S)-3,5-dimethylpiperazine-1-yl)methyl)phenyl)-4-(6-methyl-1H-indol-3-yl) pyrimidin-2-amine; or a pharmaceutically acceptable salt thereof or a hydrate thereof.

In the pharmaceutical composition for the treatment of acute myeloid leukemia according to one embodiment, the FLT3 inhibitor, or a pharmaceutically acceptable salt or solvate thereof, may be administered simultaneously, sequentially, in reverse order, or separately with the chemotherapeutic agent, or a pharmaceutically acceptable salt or solvate thereof.

In the pharmaceutical composition for the treatment of acute myeloid leukemia according to one embodiment, the FLT3 inhibitor, or a pharmaceutically acceptable salt or solvate thereof, and a chemotherapeutic agent, or a pharmaceutically acceptable salt or solvate thereof may each be included in a therapeutically effective amount.

As used herein, the term "therapeutically effective amount" is an amount of a compound that, when administered to a subject or patient in combination with a FLT3 inhibitor and a chemotherapeutic agent, treats acute myeloid leukemia.

A therapeutically effective amount in the pharmaceutical composition is an amount of a compound that does not completely inhibit the biological activity of the intended target over time when administered to a patient; it may vary within wide tolerances and may be determined in a manner known in the art. The dosage will be adjusted to the individual requirements of each particular case, including the patient to be treated as well as the specific compound to be administered, the route of administration (oral administration, parenteral administration), and the condition to be treated.

An amount proven to be a therapeutically effective amount at any moment for a particular subject may not be effective for 100% of subjects similarly treated for that disease, even if such a dose would be considered a therapeutically effective amount by a clinician. The amount of compound corresponding to a therapeutically effective amount may depend on the specific type of cancer, the stage of the cancer, the age of the patient being treated, and other factors. In general, therapeutically effective amounts of these compounds are well known in the art.

The route of administration of the pharmaceutical composition according to one embodiment includes oral, intravenous, intraarterial, intraperitoneal, intradermal, transdermal, intrathecal, intramuscular, intranasal, transmucosal, subcutaneous and rectal administration; however, it is not limited thereto.

In the pharmaceutical composition, the FLT3 inhibitor may be 5-chloro-N-(3-cyclopropyl-5-(((3R,5S)-3,5-dimethylpiperazine-1-yl)methyl)phenyl)-4-(6-methyl-1H-indole-3-yl) pyrimidin-2-amine; a pharmaceutically acceptable salt or solvate thereof; for example, the FLT3 inhibitor may be administered orally.

In the pharmaceutical composition, the chemotherapeutic agent may be 4-amino-1-[(2R,3S,4S,5R)-3,4-dihydroxy-5-(hydroxymethyl)oxolan-2-yl]pyrimidin-2-one (ingredient name: cytarabine, AraC); a pharmaceutically acceptable salt or solvate thereof; for example, the chemotherapeutic agent may be administered by intravenous injection, intraperitoneal injection, or subcutaneous injection.

In the pharmaceutical composition, the chemotherapeutic agent may be ((8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione (ingredient name: daunorubicin: DNR); a pharmaceutically acceptable salt or solvate thereof; for example, the chemotherapeutic agent may be administered by intravenous injection, intraperitoneal injection, or subcutaneous injection.

In the pharmaceutical composition, the chemotherapeutic agent may be (1S,3S)-3-Acetyl-3,5,12-trihydroxy-6,11-dioxo-1,2,3,4,6,11-hexahydrotetracene-1-yl 3-amino-2,3,6-trideoxo-α-L-ilso-hexopyranoside (ingredient name: idarubicin: IDR); a pharmaceutically acceptable salt or solvate thereof; for example, the chemotherapeutic agent may be administered by intravenous injection, intraperitoneal injection, or subcutaneous injection.

In the pharmaceutical composition, the FLT3 inhibitor may be administered in an amount of 6 mg to 600 mg. Alternatively, the FLT3 inhibitor may be administered in an amount of 0.1 mg to 10 mg/kg body weight/day. Alternatively, the FLT3 inhibitor may be administered in an amount of a body surface area of 3.7 $mg/m^2$ to 370 $mg/m^2$.

The amount of combined drug to be administered to a patient can be determined by the attending diagnostician of skill in the art using known techniques and observing the results obtained under similar circumstances. In determining an effective amount or dose of a compound to be administered, a number of factors are considered by the attending diagnostician, including but not limited to the mammalian species; its size, age and overall health; specific neoplasms involved; the extent or involvement or severity of the neoplasm; individual patient response; the particular compound being administered; the mode of administration; the bioavailability characteristics of the agent being administered; chosen usage; the use of concomitant medications; and other relevant environments. For example, when administered orally, the daily dose may be from about 0.001 to about 100 mg/kg, for example, from about 0.005 to about 30 mg/kg, for example, from about 0.01 to about 10 mg/kg, of the patient's body weight. When administered intravenously, the daily dose may suitably be from about 0.0001 to about 81 mg/kg of the patient's body weight; the whole is administered in divided doses of one or more doses per day. In addition, the transmucosal formulation is administered at a dose of about 0.001 to about 81 mg/kg per body weight; it may be administered once per day or may be administered in divided doses several times per day. For example, cytarabine may be administered in an amount of about 27 to about 81 mg per day.

The daily dose of the chemotherapeutic agent according to one embodiment is from about 0.001 to about 100 mg/kg, for example from about 0.01 to about 90 mg/kg, for example from about 0.1 to about 80 mg/kg, of the patient's body weight, or about 1 to about 50 mg/kg; it may be administered orally, intravenously or intraperitoneally.

The daily dose of the chemotherapeutic agent according to one embodiment may be 1-500 mg/m$^2$, 10-200 mg/m$^2$, or 30-45 mg/m$^2$ based on the patient's body surface area. The daily dose may be administered once a day or may be administered in divided doses. The daily dose according to one embodiment may be adjusted according to the number and type of concomitant drugs.

As a chemotherapeutic agent according to one embodiment, 4-amino-1-[(2R,3S,4S,5R)-3,4-dihydroxy-5-(hydroxymethyl)oxolane-2-yl]pyrimidin-2-one (ingredient name: cytarabine, cytarabine, AraC) may be administered in a dose of about 100 mg per m$^2$ of patient body surface area to about 200 mg per m$^2$ of patient body surface area, for example, in an amount of about 100 mg/m$^2$ to about 200 mg/m$^2$. The recommended starting dose for monotherapy, for all patients irrespective of baseline hematological values, is cytarabine 200 mg/m$^2$ per day for 5 days (120 hours) by subcutaneous (SC) injection or intravenous (IV) infusion. The treatment cycle may be repeated every two weeks.

((8S,10S)-8-acetyl-10-[(2S,4S,5S,6S)-4-amino-5-hydroxy-6-methyl-oxan-2-yl]oxy-6,8,11-trihydroxy-1-methoxy-9,10-dihydro-7H-tetracene-5,12-dione (ingredient name: daunorubicin: DNR) may be administered in a dose of about 45 mg per 1 m$^2$ of the patient's body surface area, for example, in an amount of about 45 mg/m$^2$. The recommended dose for combination therapy, for all patients irrespective of baseline hematologic values, is cytarabine 100 mg/m 2 per day for 7 days (days 1-7) administered by subcutaneous (SC) injection or intravenous (IV) infusion; and daunorubicin 45 mg/m$^2$ for 3 days (days 1-3) administered by subcutaneous (SC) injection or intravenous (IV) infusion. If the disease persists, the above combination therapy may be repeated at intervals of 2 to 4 weeks.

The dosage of the pharmaceutical composition according to one embodiment, or the dosage or therapeutically effective amount of the FLT3 inhibitor and the chemotherapeutic agent in the composition, may vary within wide tolerances; it can be determined in a manner known in the art. The dosage will be adjusted to the individual requirements of each particular case, including the patient to be treated as well as the specific compound to be administered, the route of administration (oral administration, parenteral administration), and the condition to be treated.

The daily dose may be administered as a single dose or as divided doses, or, in the case of parenteral administration, may be given as a continuous infusion.

In the pharmaceutical composition according to one embodiment, the FLT3 inhibitor and the chemotherapeutic agent may be administered simultaneously, sequentially, or separately without a specific time limit. Herein such administration is meant to provide therapeutically effective levels of the two compounds in the body of the patient. The interval between administration may be several seconds, several minutes, several hours, or number of days of a predetermined interval, and may be paused if necessary.

One aspect of the invention encompasses the administration or use of the combination at therapeutically effective intervals. A therapeutically effective interval is a period of time that begins when one of the compounds is administered to a patient and ends at the dose limit of the other compound at which the benefit of administering the two compounds in combination is maintained. Accordingly, the combined administration may be simultaneous, sequential or in any order.

The period of time or cycle of co-administration may total 1 week, 28 days, 1 month, 2 months, 3 months, or 4 months, or more. The individual drugs may each be administered daily for the entire duration or only a portion of a period or cycle. For example, in a 28 day cycle, the FLT3 inhibitor or a pharmaceutically acceptable salt or hydrate thereof may be administered daily in the cycle, whereas the chemotherapeutic agent or a pharmaceutically acceptable salt or hydrate thereof may be administered for a portion thereof, such as for 5 consecutive days, 7 consecutive days, or 10 consecutive days; the 5, 7, and 10 consecutive days may be the first 5, 7, or 10 days of a period or cycle, respectively. Alternatively, for example, the FLT3 inhibitor may be administered once a day for 21 consecutive days, and the chemotherapeutic agent may be administered 3 times a week or 5 times a week during the same period. When administered as two or more chemotherapeutic agents, each chemotherapeutic agent may have a different dosing cycle. For example, when a combination of cytarabine and daunorubicin is administered together with the FLT3 inhibitor, the FLT3 inhibitor is administered once a day for a total administration period of 21 days; during the same period, cytarabine may be administered 5 times a week, and daunorubicin may be administered 3 times a week.

The pharmaceutical composition according to one embodiment may be included in any pharmaceutically acceptable amount for simultaneous, sequential or separate use, as a medicament for the treatment of acute myeloid leukemia (AML) including the FLT3 inhibitor, or any pharmaceutically acceptable salt or hydrate thereof, and a chemotherapeutic agent, or any pharmaceutically acceptable salt or hydrate thereof.

The pharmaceutical composition may further include one or more optional pharmaceutically acceptable additives selected from the group consisting of excipients, binders, disintegrants, lubricants, and any combination thereof. The excipient is any substance known to those skilled in the art to be useful for preparing formulations, and may be adjusted as necessary, for example, according to the mode of administration of the drug.

Another aspect of the present invention provides, as a pharmaceutical composition comprising a chemotherapeutic agent, or a pharmaceutically acceptable salt or solvate thereof, a pharmaceutical composition for the treatment of acute myeloid leukemia (AML), which is administered in combination with an Fms-like tyrosine kinase (FLT3) inhibitor, or a pharmaceutically acceptable salt or solvate thereof.

In this case, the FLT3 inhibitor may be a compound selected from the compound of Formula 1, stereoisomers, tautomers, and combinations thereof.

Another aspect of the present invention provides a pharmaceutical combination (or combination) for the treatment of acute myeloid leukemia (AML), including an FLT3 inhibitor, a pharmaceutically acceptable salt thereof, or a solvate thereof; and a chemotherapeutic agent, a pharmaceutically acceptable salt, or solvate thereof; in this case, the FLT3 inhibitor is a compound selected from the compound of Formula 1, stereoisomers, tautomers, and combinations thereof.

In the pharmaceutical combination, the FLT3 inhibitor, or a pharmaceutically acceptable salt thereof, or a solvate including a hydrate, etc.; and the two active ingredients of a solvate including a chemotherapeutic agent, or a pharmaceutically acceptable salt or hydrate thereof; may be administered simultaneously, sequentially or separately.

As used herein, the term "combination" or "pharmaceutical combination" means a product produced by mixing or combining two or more active ingredients, and includes both fixed and non-fixed combinations of active ingredients. The term "fixed combination" means that an active ingredient, eg, a compound disclosed herein, and one or more additional therapeutic agents are administered to a subject simultaneously in the form of a single aggregate or dosage. The term "non-fixed combination" means that an active ingredient, such as a compound disclosed herein, and one or more additional therapeutic agents are administered to the subject simultaneously, concurrently or sequentially as separate aggregates without any specific time limit; wherein such administration provides a therapeutically effective level of the active ingredient in the subject's body. The latter can also be applied to cocktail therapy, for example, administration of three or more active ingredients.

Another aspect of the present invention provides a pharmaceutical kit including instructions for administering the pharmaceutical composition or pharmaceutical combination simultaneously, sequentially or separately.

The kit may include instructions including, for example, dosing schedules that optionally, allow a practitioner (e.g., doctor, nurse) or patient to administer the composition or combination contained therein to a patient having cancer such as acute myeloid leukemia (AML). The kit may also include a syringe.

Another aspect of the present invention provides a treatment method for treating acute myeloid leukemia (AML) using the pharmaceutical composition, pharmaceutical combination, or kit. In this case, the active ingredients may be administered simultaneously, sequentially or separately.

The FLT3 inhibitor, or a pharmaceutically acceptable salt, or hydrate thereof; and chemotherapeutic agent, or a composition comprising a pharmaceutically acceptable salt or hydrate thereof as an active ingredient, may be used to treat a subject suffering from acute myeloid leukemia (AML).

A subject to be treated according to the method of treatment includes a subject suffering from acute myeloid leukemia having a FLT3 mutation. For example, the acute myeloid leukemia includes a mutant FLT3 polynucleotide-positive myeloid leukemia, a columnar duplication (ITD) positive acute myeloid leukemia in the FLT3 gene, or an acute myeloid leukemia having an FLT3 point mutation.

As used herein, the term "subject" encompasses mammals and non-mammals, including humans. Examples of mammals include humans, chimpanzees, apes, monkeys, cattle, horses, sheep, goats, pigs; rabbits, dogs, cats, rats, mice, guinea pigs, and the like. Examples of non-mammals include, but are not limited to, birds, fish, and the like.

As used herein, the terms "treating," "treat," "to treat," or "treatment" include limiting, delaying, arresting, reducing or reversing the progression or severity of an existing symptom, disease, condition, or disorder.

One aspect of the present invention provides the use of a combination including an FLT3 inhibitor, or a pharmaceutically acceptable salt, or solvate thereof; or a chemotherapeutic agent, or a pharmaceutically acceptable salt or solvate thereof; as an active ingredient used in the manufacture of a drug for the treatment of acute myeloid leukemia (AML).

The pharmaceutical composition, pharmaceutical combination, pharmaceutical kit, and method of treatment may use the previously described components of the chemotherapeutic agents, FLT3 inhibitors, or pharmaceutically acceptable salts thereof; or solvates thereof, these dosages and administration methods.

The combination therapy of a FLT3 inhibitor and a chemotherapeutic agent using the pharmaceutical composition, pharmaceutical combination, pharmaceutical kit, and treatment method of one aspect according to the present invention have improved therapeutic effects compared to the effects when the FLT3 inhibitor or the chemotherapeutic agent is administered alone. The therapeutic effect according to one embodiment represents a synergistic therapeutic effect greater than the arithmetic sum of two or more drugs used in combination.

The industrial applicability herein is exemplified by the positive impact in one or more studies, including the description of one or more parameters, of the utility of this combination therapy.

Hereinafter, the present invention will be described in more detail by way of Working Examples and Experimental Examples. However, these Working Examples and Experimental Examples are only for helping the understanding of the present invention, and the scope of the present invention is not limited thereto in any sense.

Working Example 1

MV-4-11 Cell Line Xenografted Mouse Model

In a mouse model xenografted with the MV-4-11 cell line, comparison or combination efficacy tests were conducted of the FLT3 inhibitor 5-Chloro-N-(3-cyclopropyl-5-(((3R,5S)-3,5-dimethylpiperazine-1-yl)methyl)phenyl)-4-(6-methyl-1H-indole-3-yl)pyrimidin-2-amine (hereinafter compound A); 4-amino-1-[(2R,3S,4S,5R)-3,4-dihydroxy-5-(hydroxymethyl)oxolane-2-yl]pyrimidin-2-one (hereafter cytarabine); and ((8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione (hereafter daunorubicin).

The MV-4-11 cell line was purchased from the American Type Culture Collection (ATCC). To construct a xenografted mouse model using this MV-4-11 cell line, 5-week-old female CAnN·Cg-Foxn1nu/Crljbgi mice (hereinafter, Nude mice) were purchased from Charles River Laboratories Japan, Inc.

The MV-4-11 cell line was inoculated subcutaneously in the flank with $5 \times 10^6$ cells/10 ml/mouse and allowed to grow. Mice having a tumor volume of 100 to 300 mm$^3$ (length× width$^2$×0.5) were selected 1 day before administration, the average tumor volume in each group was divided into 4 groups (5 animals/group) so that the average tumor volume was almost the same, and each dose was administered for a total period of 21 days.

The control group received DMSO/PEG400/DW (ratio=0.5/2/7.5, v/v/v) mixed solution orally once a day; the Compound A group was orally administered once a day at a dose of 3 mg/kg/day from days 1 to 21; the CTx (cytarabine+Daunorubicin) group received intraperitoneal administration of cytarabine at a dose of 50 mg/kg/day 5 times a week (weekly 1 st–5th day: cytarabine) from the 1st to the 21$^{st}$ days; daunorubicin was administered intravenously at a dose of 2 mg/kg/day 3 times a week (weekly 1st-3rd day: daunorubicin). In the combination group, Compound A was orally administered once a day at a dose of 3 mg/kg/day from days 1 to 21; the CTx (Cytarabine+Daunorubicin) group received the intraperitoneal administration of cytarabine at a dose of 50 mg/kg/day 5 times a week (weekly 1st-5th day: cytarabine) from the 1st to the $21^{st}$, and daunorubicin was administered intravenously at a dose of 2 mg/kg/day 3 times a week (weekly 1st-3rd day: daunorubicin).

The experimental results are shown in The FIGURE. The FIGURE shows the tumor volume (mm 3) measured after treatment with each treatment solution or drug alone or in combination in nude mice xenografted with the MV-4-11 cell line. From the results of The FIGURE, the antitumor effect when the FLT3 inhibitor and the chemotherapeutic agent are administered in combination can be seen. The Y-axis represents the mean tumor volume ($mm^3$) and the X-axis represents the number of days of dosing. Tumor growth inhibition (TGI) was calculated from "(1-(average tumor volume of drug-treated group)/(average tumor volume of control group))×100%." Here, the average of the tumor volumes of each of 5 Nude mice used in each treatment group was taken as the average tumor volume.

As shown in The FIGURE, the average tumor volume was measured for a period of 21 days of drug dosing in each treatment group; from this, the effect of tumor growth inhibition (TGI) was obtained. As a result, compared with the group administered only with Compound A (Compound A group) or the group administered only with the chemotherapeutic agent (Cytarabine+Daunorubicin (CTx) group), the average tumor volume in the combined group was significantly reduced. The tumor growth inhibitory (TGI) effect was increased in the combination group (TGI=75.8% in the combination group, TGI=34.7% in the compound A group, TGI=34.1% in the CTx group).

From the experimental results using the mouse efficacy model xenografted with MV4-11 cells shown in The FIGURE, compared to the group administered only with the FLT3 inhibitor Compound A or the group administered only with chemotherapeutic agents (Cytarabine and Daunorubicin), it was confirmed that in the combination group of the FLT3 inhibitor and chemotherapeutic agents (cytarabine and daunorubicin) the decrease in average tumor volume increased and improved antitumor efficacy was exhibited.

Industrial applicability of the utility of this combination therapy is exemplified by the positive impact in one or more studies, including the description of one or more parameters.

So far, the present invention has been focused on specific examples thereof; those of ordinary skill in the art pertaining to the present invention will understand that the present invention can be implemented in a modified form without departing from the essential characteristics of the present invention. Therefore, the disclosed embodiments are to be considered in an illustrative rather than a restrictive sense. The scope of the present invention is indicated in the claims rather than the foregoing description, and all differences within the scope equivalent thereto should be construed as being included in the present invention.

The invention claimed is:

1. A pharmaceutical combination comprising a compound of Formula 1, a stereoisomer thereof, a tautomer thereof, or a combination thereof, or a pharmaceutically acceptable salt thereof, or a solvate thereof, and
one or more chemotherapeutic agents, or a pharmaceutically acceptable salt thereof, or solvate thereof; wherein:

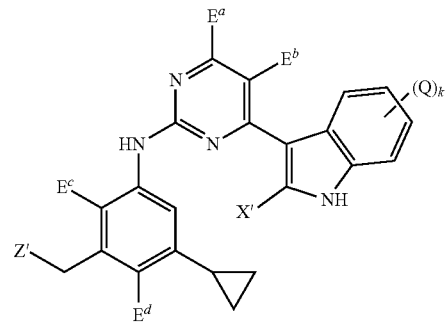

[Formula 1]

in Formula 1,
$E^a$ is hydrogen, hydroxy or $C_{1-4}$ alkoxy;
$E^b$ is hydrogen, halogen, $C_{1-4}$ alkyl or $C_{1-4}$ fluoroalkyl;
$E^c$ and $E^d$ are independently of each other hydrogen or hydroxy;
X' is hydrogen or hydroxy;
k is an integer from 1 to 2;
each Q is independently of the other hydroxy, halogen, $C_{1-4}$ alkyl, hydroxy$C_{1-4}$ alkyl or $C_{1-4}$ alkoxy;
Z' is a monovalent functional group shown in formula (2);

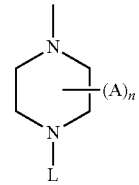

[Formula 2]

in this case, in Formula 2, n is an integer of 1 to 2;
each A is, independently of the other, a functional group selected from hydroxy, $C_{1-4}$ alkyl and hydroxy$C_{1-4}$ alkyl, wherein at least one A is $C_{1-4}$ alkyl; and
L is hydrogen, $C_{1-4}$ alkyl, hydroxy or hydroxy $C_{1-4}$ alkyl.

2. The pharmaceutical combination of claim 1, wherein the compound of Formula 1 is a compound of Formula 3, or a stereoisomer thereof, tautomer thereof, or a combination thereof, or a pharmaceutically acceptable salt thereof, or a solvate thereof; wherein

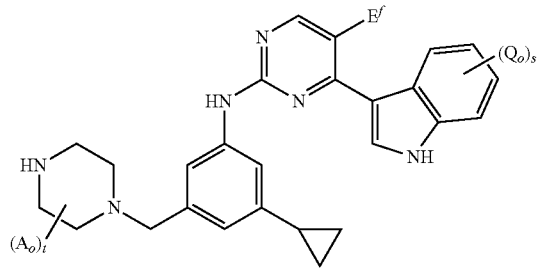

[Formula 3]

in Formula 3,
$E^f$ is fluorine, chlorine, bromine or iodine;
$Q_o$ is hydroxy, halogen, C 1-4 alkyl, hydroxy C1-4 alkyl or C 1-4 alkoxy;

s is an integer from 1 to 2;

A_o is a functional group selected from hydroxy, C 1-4 alkyl and hydroxy C1-4 alkyl; and t is an integer from 1 to 2.

3. The pharmaceutical combination of claim 2, wherein the compound of Formula 3 is 5-chloro-N-(3-cyclopropyl-5-(((3R,5S)-3,5-dimethylpiperazine-1-yl)methyl)phenyl)-4-(6-methyl-1H-indole-3-yl) pyrimidin-2-amine; or a pharmaceutically acceptable salt thereof, a stereoisomer thereof, or a hydrate thereof.

4. The pharmaceutical combination of claim 1, wherein the chemotherapeutic agent is one or more of 4-amino-1-[(2R,3S,4S,5R)-3,4-dihydroxy-5-(hydroxymethyl)oxolane-2-yl]pyrimidin-2-one; (8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione; or a pharmaceutically acceptable salt thereof, or solvate thereof.

5. The pharmaceutical combination of claim 1, wherein the chemotherapeutic agent is one or more of 4-amino-1-[(2R,3S,4S,5R)-3,4-dihydroxy-5-(hydroxymethyl)oxolan-2-yl]pyrimidin-2-one; (8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione; or a pharmaceutically acceptable salt thereof, or hydrate thereof.

6. The pharmaceutical combination of claim 2, wherein the chemotherapeutic agent is one or more of 4-amino-1-[(2R,3S,4S,5R)-3,4-dihydroxy-5-(hydroxymethyl)oxolane-2-yl]pyrimidin-2-one; (8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione; or a pharmaceutically acceptable salt thereof, or hydrate thereof.

7. The pharmaceutical combination of claim 6, wherein the chemotherapeutic agent is one or more of 4-amino-1-[(2R,3S,4S,5R)-3,4-dihydroxy-5-(hydroxymethyl)oxolane-2-yl]pyrimidin-2-one; (8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione; or a pharmaceutically acceptable salt thereof, or a hydrate thereof; and the compound of Formula 1 is 5-chloro-N-(3-cyclopropyl-5-(((3R,5S)-3,5-dimethylpiperazine-1-yl)methyl)phenyl)-4-(6-methyl-1H-indol-3-yl)pyrimidin-2-amine or a pharmaceutically acceptable salt thereof, stereoisomer thereof, or hydrate thereof.

8. The pharmaceutical combination of claim 1, wherein the chemotherapeutic agents are 4-amino-1-[(2R,3S,4S,5R)-3,4-dihydroxy-5-(hydroxymethyl)oxolane-2-yl]pyrimidin-2-one; and (8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione; or a pharmaceutically acceptable salt thereof, or a hydrate thereof.

9. The pharmaceutical combination of claim 8, wherein the chemotherapeutic agents are 4-amino-1-[(2R,3S,4S,5R)-3,4-dihydroxy-5-(hydroxymethyl)oxolane-2-yl]pyrimidin-2-one; and ((8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione.

10. The pharmaceutical combination of claim 2, wherein the chemotherapeutic agents are 4-amino-1-[(2R,3S,4S,5R)-3,4-dihydroxy-5-(hydroxymethyl)oxolane-2-yl]pyrimidin-2-one; and (8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione; or a pharmaceutically acceptable salt thereof, or a hydrate thereof.

11. The pharmaceutical combination of claim 10, wherein the chemotherapeutic agents are 4-amino-1-[(2R,3S,4S,5R)-3,4-dihydroxy-5-(hydroxymethyl)oxolan-2-yl]pyrimidin-2-one; and ((8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione.

12. The pharmaceutical combination of claim 1, wherein the chemotherapeutic agents are 4-amino-1-[(2R,3S,4S,5R)-3,4-dihydroxy-5-(hydroxymethyl)oxolane-2-yl]pyrimidin-2-one; and ((8S,10S)-8-acetyl-10-[(2S,4S,5S,6S)-4-amino-5-hydroxy-6-methyl-oxane-2-yl]oxy-6,8,11-trihydroxy-1-methoxy-9,10-dihydro-7H-tetracene-5,12-dione;

and the compound of Formula 1 is 5-chloro-N-(3-cyclopropyl-5-(((3R,5S)-3,5-dimethylpiperazine-1-yl)methyl)phenyl)-4-(6-methyl-1H-indol-3-yl)pyrimidin-2-amine, or a pharmaceutically acceptable salt thereof, stereoisomer thereof, or hydrate thereof.

13. The pharmaceutical combination of claim 1, wherein the compound of Formula 1, or a stereoisomer thereof, a tautomer thereof, or a combination thereof, or a pharmaceutically acceptable salt thereof, or solvate thereof, and the chemotherapeutic agent, or a pharmaceutically acceptable salt or solvate thereof are in the same dosage form.

14. The pharmaceutical combination of claim 1, wherein the compound of Formula 1 is selected from the group consisting of:

| No. | Name of Compound |
|---|---|
| 1 | 5-chloro-N-(3-cyclopropyl-5-(((3R,5S)-3,5-dimethylpiperazine-1-yl)methyl)phenyl)-4-(6-fluoro-1H-indol-3-yl)pyrimidine-2-amine |
| 2 | 5-chloro-5-(6-chloro-1H-indol-3-yl)-N-(3-cyclopropyl-5-(((3R,5S)-3,5-dimethylpiperazine-1-yl)methyl)phenyl)pyrimidine-2-amine |
| 3 | 2-((2R,6S)-4-(3-((5-chloro-4-(6-fluoro-1H-indol-3-yl)pyrimidine-2-yl)amino)-5-cyclopropylbenzyl)-2,6-dimethylpiperazine-1-yl)ethan-1-ol |
| 4 | 2-((2R,6S)-4-(3-((5-chloro-4-(1H-indol-3-yl)pyrimidine-2-yl)amino)-5-cyclopropylbenzyl)-2,6-dimethylpiperazine-1-yl)ethan-1-ol |
| 5 | 2-((2R,6S)-4-(3-((5-chloro-4-(6-methyl-1H-indol-3-yl)-pyrimidine-2-yl)amino)-5-cyclopropylbenzyl)-2,6-dimethylpiperazine-1-yl)ethan-1-ol |
| 6 | (R)-5-chloro-N-(3-cyclopropyl-5-((3-methylpiperazine-1-yl)methyl)phenyl)-4-(1H-indol-3-yl)-pyrimidine-2-amine |
| 7 | (R)-5-chloro-N-(3-cyclopropyl-5-((3-methylpiperazine-1-yl)methyl)phenyl)-4-(6-methyl-1H-indol-3-yl)pyrimidine-2-amine |
| 8 | 5-chloro-N-(3-cyclopropyl-5-(((3R,5S)-3,5-dimethylpiperazine-1-yl)methyl)phenyl)-4-(6-methyl-1H-indol-3-yl)pyrimidine-2-amine |
| 9 | 5-chloro-N-(3-cyclopropyl-5(((3S,5R)-3-ethyl-5-methylpiperazine-1-yl)methyl)phenyl)-4-(6-methyl-1H-indol-3-yl)pyrimidine-2-amine |

| No. | Name of Compound |
|---|---|
| 10 | 5-chloro-N-(3-cyclopropyl-5-((3,5-dimethylpiperazine-1-yl)methyl)phenyl)-4-(6-methyl-1H-indol-3-yl)pyrimidine-2-amine |
| 11 | N-(3-cyclopropyl-5-(((3R,5S)-3,5-dimethylpiperazine-1-yl)methyl)phenyl)-5-fluoro-4-(6-methyl-1H-indol-3-yl)pyrimidine-2-amine |
| 12 | N-(3-cyclopropyl-5-(((3R,5S)-3,5-dimethylpiperazine-1-yl)methyl)phenyl)-5-fluoro-4-(6-methyl-1H-indol-3-yl)pyrimidine-2-amine |
| 13 | N-(3-cyclopropyl-5-(((3R,5S)-3,5-dimethylpiperazine-1-yl)methyl)phenyl)-4-(1H-indol-3-yl)-5-methylpyrimidine-2-amine |
| 14 | N-(3-cyclopropyl-5-(((3R,5S)-3,5-dimethylpiperazine-1-yl)methyl)phenyl)-5-methyl-4-(6-methyl-1H-indol-3-yl)pyrimidine-2-amine |
| 15 | N-(3-cyclopropyl-5-(((3R,5S)-3,5-dimethylpiperazine-1-yl)methyl)phenyl)-4-(6-methyl-1H-indol-3-yl)-5-(trifluoromethyl)pyrimidine-2-amine |
| 16 | (3-(5-chloro-2-((3-cyclopropyl-5-(((3R,5S)-3,5-dimethylpiperazine-1-yl)methyl)phenyl)amino)pyrimidine-4-yl)-1H-indol-6-yl)methanol |
| 17 | 5-chloro-N-(3-cyclopropyl-5-(((3R,5S)-3,5-dimethylpiperazine-1-yl)methyl)phenyl)-4-(5-methoxy-6-methyl-1H-indol-3-yl)pyrimidine-2-amine |
| 18 | 3-(5-chloro-4-((3-cyclopropyl-5-(((3R,5S)-3,5-dimethylpiperazine-1-yl)methyl)phenyl)amino)pyrimidine-4-yl)-6-methyl-1H-indol-5-ol |
| 19 | 3-(5-chloro-2-((3-cyclopropyl-5-(((3R,5S)-3,5-dimethylpiperazine-1-yl)methyl)phenyl)amino)pyrimidine-4-yl)-6-methylindoline-2-on |
| 20 | 5-chloro-N-(3-cyclopropyl-5-(((3R,5S)-3,5-dimethylpiperazine-1-yl)methyl)phenyl)-4-methoxy-6-(6-methyl-1H-indol-3-yl)pyrimidine-2-amine |
| 21 | 5-chloro-2-((3-cyclopropyl-5-(((3R,5S)-3,5-dimethylpiperazine-1-yl)methyl)phenyl)amino)-6-(6-methyl-1H-indol-3-yl)pyrimidine-4-ol |
| 22 | 3-(5-chloro-2-((3-cyclopropyl-5-(((3R,5S)-3,5-dimethylpiperazine-1-yl)methyl)phenyl)amino)pyrimidine-4-yl)-6-methyl)-1H-indol-7-ol |
| 23 | 2-((5-chloro-4-(6-methyl-1H-indol-3-yl)pyrimidine-2-yl)amino)-4-cyclopropyl-6-(((3R,5S)-3,5-dimethylpiperazine-1-yl)methyl)phenol |
| 24 | 4-((5-chloro-4-(6-methyl-1H-indol-3-yl)pyrimidine-2-yl)amino)-2-cyclopropyl-6-(((3R,5S)-3,5-dimethylpiperazine-1-yl)methyl)phenol |
| 25 | (R)-5-chloro-N-(3-cyclopropyl-5-((3,3,5-trimethylpiperazine-1-yl)methyl)phenyl)-4-(6-methyl-1H-indol-3-yl)pyrimidine-2-amine |
| 26 | ((2R,6R)-4-(3-((5-chloro-4-(6-methyl-1H-indol-3-yl)pyrimidine-2-yl)amino)-5-cyclopropylbenzyl)-6-methylpiperazine-2-yl)methanol |
| 27 | (R)-5-chloro-N-(3-cyclopropyl-5-((5-methyl-4,7-diazaspiro[2,5]octan-7-yl)methyl)phenyl)-4-(6-methyl-1H-indol-3-yl)pyrimidine-2-amine |
| 28 | 5-chloro-N-(3-cyclopropyl-5-(((3R,5R)-3,5-dimethylpiperazine-1-yl)methyl)phenyl)-4-(6-methyl)-1H-indol-3yl)-pyrimidine-2-amine |
| 29 | 5-chloro-N-(3-cyclopropyl-5-(((3S,5S)-3,5-dimethylpiperazine-1-yl)methyl)phenyl)-4-(6-methyl-1H-indol-3-yl)pyrimidine-2-amine |
| 30 | 5-chloro-N-(3-cyclopropyl-5-(((3R,5S)-3 4,5-trimethylpiperazine-1-yl)methyl)phenyl)-4-(6-methyl-1H-indol-3-yl)pyrimidine-2-amine |
| 31 | (2R,6S)-4-(3-((5-chloro-4-(6-methyl-1H-indol-3-yl)pyrmidine-2-yl)amino)-5-cyclopropylbenzyl)-2,6-dimethylpiperazine-1-ol |
| 32 | (2R,6S)-4-(3-cyclopropyl-5-((4-(6-methyl-1H-indol-3-yl)-pyrimidine-2-yl)amino)benzyl)-2,6-dimethylpiperazine-1-ol. |

15. A pharmaceutical combination of claim 1, wherein the pharmaceutical combination comprises a compound of Formula 1 and one or more chemotherapeutic agents in separate dosage forms.

16. A method of treating acute myeloid leukemia (AML) in a subject in need thereof, comprising administering to the subject a pharmaceutical combination of claim 1, wherein the pharmaceutical combination comprises a compound of Formula 1 and one or more chemotherapeutic agents in separate dosage forms.

17. The method of claim 16, wherein the acute myeloid leukemia is an acute myeloid leukemia having a FLT3 mutation.

18. The method of claim 16, wherein the acute myeloid leukemia is mutant FLT3 polynucleotide-positive acute myeloid leukemia, FLT3 internal tandem duplication (ITD) positive acute myeloid leukemia, or acute myeloid leukemia with a FLT3 point mutation.

19. The method of claim 17, wherein, the acute myeloid leukemia (AML) has a mutation in a tyrosine kinase domain (TKD) (FLT3-TKD) of the FLT3 amino acid sequence.

20. The method of claim 19, wherein the FLT3-TKD mutation further includes an internal tandem duplication (ITD).

21. The method of claim 19, wherein the FLT3-TKD mutation includes any one selected from FLT3 (D835Y), FLT3 (F691L), FLT3 (F691L/D835Y), FLT3 (ITD/D835Y), FLT3 (ITD/F691L), and combinations thereof.

* * * * *